United States Patent [19]

Zoller et al.

[11] Patent Number: 4,666,902

[45] Date of Patent: May 19, 1987

[54] TETRAHYDROPYRIDAZINONE DERIVATIVES, PROCESSES FOR THEIR PREPARATION AND THEIR USE

[75] Inventors: Gerhard Zoller, Maintal; Rudi Beyerle, Frankfurt; Melitta Just, Schöneck; Piero Martorana, Bad Homburg; Helmut Bohn, Schöneck; Rolf-Eberhard Nitz, Frankfurt, all of Fed. Rep. of Germany

[73] Assignee: Cassella Aktiengesellschaft, Fed. Rep. of Germany

[21] Appl. No.: 618,526

[22] Filed: Jun. 8, 1984

[30] Foreign Application Priority Data

Jun. 20, 1983 [DE] Fed. Rep. of Germany ....... 3322079
Mar. 30, 1984 [DE] Fed. Rep. of Germany ....... 3411850

[51] Int. Cl.⁴ .................. C07D 237/02; C07D 401/04; C07D 403/04; A61K 31/50
[52] U.S. Cl. .................. 514/212; 514/218; 514/222; 514/226; 514/230; 514/228; 514/229; 514/231; 514/232; 514/234; 514/235; 514/247; 514/252; 514/253; 540/460; 540/492; 540/524; 540/525; 544/3; 544/54; 544/56; 544/58.2; 544/58.6; 544/61; 544/63; 544/66; 544/67; 544/68; 544/72; 544/82; 544/96; 544/98; 544/114; 544/182; 544/215; 544/220; 544/222; 544/223; 544/238; 544/239
[58] Field of Search ...................... 544/238, 239, 3, 56, 544/54, 58.2, 58.6, 61, 63, 66, 67, 68, 82, 72, 96, 114, 98, 182, 215, 220, 222, 223; 260/243.3; 540/460, 492, 524, 525; 514/212, 218, 222, 226, 230, 228, 231, 232, 229, 234, 235, 242, 252, 253

[56] References Cited

U.S. PATENT DOCUMENTS

| 4,055,644 | 10/1977 | Houlihan | 544/239 |
| 4,404,203 | 9/1983 | Sircar | 544/239 |
| 4,521,416 | 6/1985 | Sircar | 544/239 |

FOREIGN PATENT DOCUMENTS

| 54-16485 | 2/1979 | Japan | 544/238 |
| 59-53479 | 3/1984 | Japan | 544/238 |

OTHER PUBLICATIONS

Wamhoff et al, Chem Abs. 71,61314t, (1969).

*Primary Examiner*—Mark L. Berch
*Attorney, Agent, or Firm*—Thomas L. Tully

[57] ABSTRACT

Tetrahydropyridazinones of the formula I

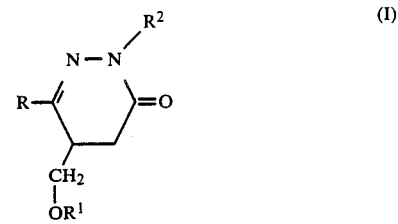

wherein R denotes an optionally substituted carbocyclic or heterocyclic radical, $R^1$ denotes hydrogen; alkyl; aralkyl, which is optionally substituted in the aryl part; or acyl, and $R^2$ denotes hydrogen; alkyl, which can optionally be substituted; or optionally substituted phenyl; and their acid addition compounds, if these can be prepared.

The tetrahydropyridazinone derivatives of the formula I according to the invention and their physiologically acceptable salts exhibit useful pharmacological actions.

14 Claims, No Drawings

TETRAHYDROPYRIDAZINONE DERIVATIVES, PROCESSES FOR THEIR PREPARATION AND THEIR USE

The present invention relates to tetrahydropyridazinones of the formula I

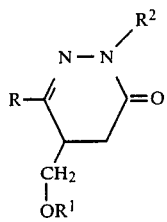
(I)

wherein R denotes one of the radicals of the formulae

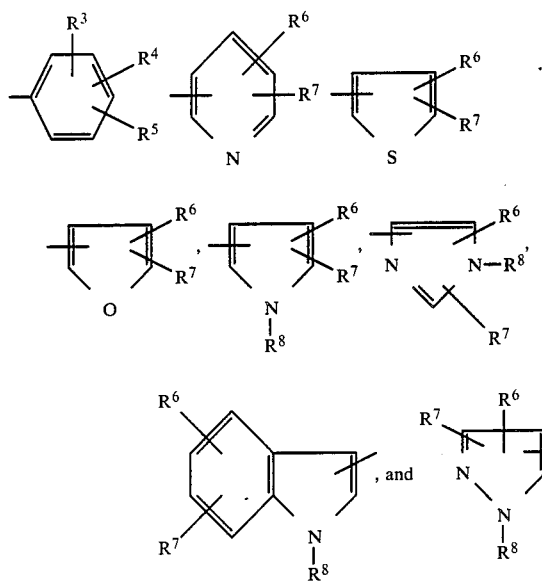

$R^1$ denotes hydrogen; alkyl; aralkyl, which is optionally substituted in the aryl part; or acyl of the formula —CO—$R^9$; $R^2$ denotes hydrogen; alkyl, which can optionally be substituted by basic groups; or optionally substituted phenyl; $R^3$, $R^4$ and $R^5$ independently of one another denote halogen; alkyl with 1 to 5C atoms; —OH; alkoxy with 1 to 5C atoms; alkanoyloxy with 1 to 5C atoms; benzoyloxy; alkylmercapto with 1 to 5C atoms; —NH$_2$; monoalkylamino with 1 to 5C atoms; dialkylamino with a total of 2 to 5C atoms; or alkanoylamino with 1 to 4C atoms; and $R^3$ and $R^4$ also denote nitro; cyano; alkylmercapto, alkylsulphoxy or alkylsulphonyl with in each case 1 to 5C atoms, alkyl—(C$_1$-C$_5$)—oxycarbonyl or a group of the formula —NR$^{10}$R$^{11}$, it being possible for alkyl, alkoxy, alkylamino, dialkylamino, alkylmercapto, alkylsulphoxy and alkylsulphonyl radicals $R^3$ and $R^4$ to be further substituted in the alkyl part by hydroxyl, alkoxy with 1 to 5, preferably 1 or 2, C atoms, carboxyl, alkoxycarbonyl with a total of 2 to 7C atoms or aminocarbonyl of the formula

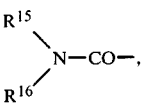

wherein $R^{15}$ and $R^{16}$ independently of one another denote hydrogen or alkyl with 1 to 5C atoms, which can in turn be substituted by alkoxy with 1 to 4C atoms, halogen, in particular chlorine or bromine, —NH$_2$ or mono- or di-alkylamino with 1 to 4C atoms in the alkyl groups, or wherein $R^{15}$ and $R^{16}$, together with the N atom to which they are bonded, form the radical of a 5-membered or 6-membered heterocyclic ring which optionally contains a further hetero-atom, such as, for example, pyrrolidine, piperidine, piperazine, alkylpiperazine, morpholine or thiomorpholine, or by amino, monoalkylamino with 1 to 5, preferably 1 or 2, C atoms, dialkylamino with a total of 2 to 6C atoms or a 5-membered or 6-membered heterocyclic radical with 1 to 3 hetero-atoms; and $R^4$ and $R^5$ additionally also denote hydrogen; $R^6$ and $R^7$ independently of one another denote hydrogen; halogen, in particular chlorine and bromine; amino, monoalkylamino with 1 to 5C atoms, dialkylamino with a total of 2 to 6C atoms, hydroxyl, alkoxy with 1 to 5C atoms or alkyl with 1 to 5C atoms; $R^8$ denotes hydrogen, alkyl with 1 to 5C atoms, alkanoyl with 1 to 5C atoms or a radical of the formula

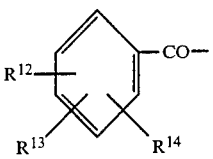

$R^9$ denotes alkyl with 1 to 5C atoms, which is optionally substituted by an optionally substituted phenoxy radical,

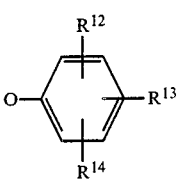

a group of the formula

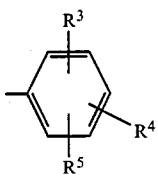

or pyridyl; $R^{10}$ denotes alkanoyl with 1 to 5C atoms, which can optionally be substituted by —OH, —NH$_2$, halogen, in particular chlorine or bromine, alkoxy with 1 to 5C atoms or phenoxy of the formula benzoyl of the formula

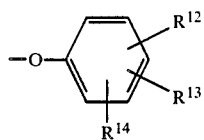

heterocycloalkylcarbonyl of the formula

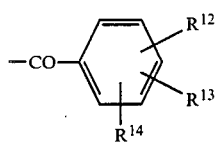

wherein n=2; 3 or 4 m=0; 1 or 2, and, preferably, $n+m=3$ or 4, and X represents oxygen, sulphur or a group of the formula $=N-R^8$, it being possible for the heterocyclic nucleus to be further substituted by alkyl with 1 to 5, preferably 1 or 2, C atoms, chlorine, bromine or double-bonded oxygen (=O), or $R^{10}$ denotes

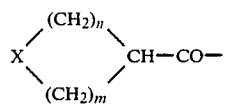

and $R^{11}$ denotes hydrogen, alkyl with 1 to 5C atoms or alkanoyl with 1 to 5C atoms, or $R^{10}$ and $R^{11}$, together with the nitrogen atom to which they are bonded, form a pyrrolidine, piperidine, piperazine, morpholine or thiomorpholine ring or a ring of the formula

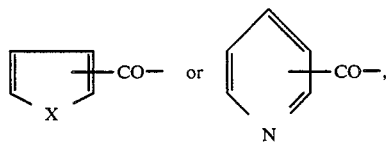

wherein p=3, 4 or 5; and q=2 or 3, or

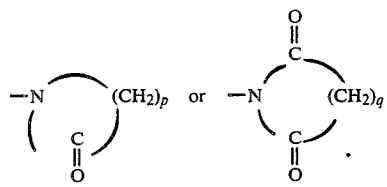

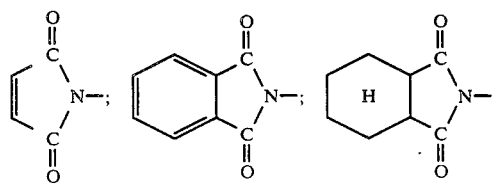

wherein r=1 or 2, or

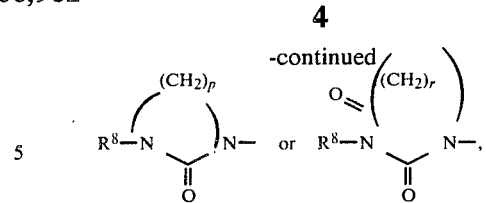

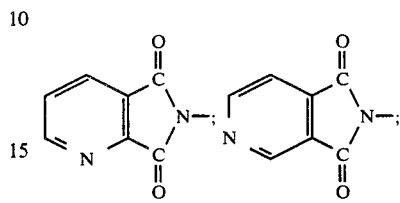

wherein u=0, 1 or 2 and t=0, 1 or 2, which can optionally be further substituted by alkyl with 1 to 5, preferably 1 or 2, C atoms, and $R^{12}$ to $R^{14}$ denote hydrogen, alkyl with 1 to 5C atoms, alkoxy with 1 to 5C atoms, nitro, cyano, halogen, in particular chlorine or bromine, amino, monoalkylamino with 1 to 5C atoms, dialkylamino with a total of 2 to 6C atoms, alkanoylamino with 1 to 5C atoms or benzoylamino, and to their acid addition compounds, if these can be prepared.

The tetrahydropyridazinone derivates of the formula I according to the invention, wherein the substituents $R^3$, $R^4$ and $R^5$ of a phenyl nucleus R have the above-mentioned meanings, and their physiologically acceptable salts exhibit useful pharmacological actions. Surprisingly, they are considerably superior to the hitherto known compounds of the same type of action.

The compounds of the formula I in which R is an unsubstituted phenyl nucleus, that is to say wherein $R^3$ also denotes hydrogen, and their physiologically acceptable salts also exhibit a similarly useful pharmacological action.

The substituents $R^3$ to $R^5$ of a radical R of the formula

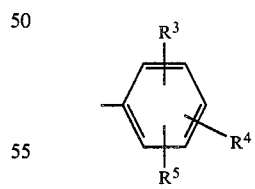

can be in any desired position of the phenyl nucleus. If $R^4$ and $R^5$ are hydrogen, $R^3$ can have the abovementioned meanings and can be in the 2-, 3- or 4-position of the phenyl nucleus. In the case of disubstitution, only $R^5$ is hydrogen, and $R^3$ and $R^4$ independently of one another have the abovementioned meanings and can be in the 2,3-; 3,2-; 2,4-; 4,2-; 2,5-; 5,2-; 2,6-; 3,4-; 4,3- or 3,5-position. Preferably, a disubstituted phenyl nucleus R has only one optionally substituted amino group and only one acyloxy group, that is to say only $R^3$ has the meanings defined above of —NH$_2$, mono- or dialkylamino or alkanoyl- or benzoyloxy. Any third substituent present ($R^5$=hydrogen) is preferably chlorine, an alkyl radical, in particular methyl, or an alkoxy radical, in particular methoxy.

5-membered or 6-membered heterocyclic radicals with 1 to 3 hetero-atoms which can be substituents of an alkyl, alkoxy, alkylamino, dialkylamino, alkylmercapto, alkylsulphoxy or alkylsulphonyl group $R^3$ or $R^4$ are aromatic or hetero-aromatic five-membered rings with 1, 2 or 3 nitrogen atoms, such as, for example, pyrrole, pyrrole N-oxide, pyrazole, imidazole, s-triazole, pyrrolidine, pyrrolidine N-oxide, pyrazoline, imidazoline and s-triazoline, five-membered rings with an oxygen atoms, such as furan and tetrahydrofuran, with a sulphur atom, such as thiophene, tetrahydrothiophene, thiophene S-oxide, tetrahydrothiophene S-oxide and tetrahydrothiophene S-dioxide, or with various hetero-atoms, such as oxazole, oxazoline, thiazole, thiazoline, oxadiazole and oxadiazoline, or aromatic or hetero-aromatic six-membered rings with 1, 2 or 3 nitrogen atoms, such as pyridine, pyridine N-oxide, piperidine, pyridazine, di-, tetra- and hexa-hydropyridazine, pyrazine, di-, tetra- and hexa-hydropyrazine, pyrimidine, di-, tetra- and hexahydropyrimidine, s-triazine and di-, tetra- and hexahydro-s-triazine, six-membered rings with one or two oxygen atoms, such as, for example, pyran, di- and tetrahydropyran, 1,3- and 1,4-dioxane, 1,3- and 1,4-dioxene and 1,4-dioxadiene, or with one or two sulphur atoms, such as thiapyran and tetrahydrothiapyran and the S-oxides and S-dioxides thereof, 1,4-dithiane, 1,4-dithiene and 1,4-dithiadiene and the S-oxides and S-dioxides thereof, or six-membered rings with various hetero-atoms, such as, for example, 1,3- and 1,4-oxazine in its tautomeric forms, dihydro-1,3- and 1,4-oxazine, morpholine, 1,3- and 1,4-thiazine, dihydro-1,3- and -1,4-thiazine, thiomorpholine, 1,4-oxathiane, 1,4-oxathiene and 1,4-oxathiadiene.

The heterocyclic radials mentioned can in turn also carry one or two, preferably one, alkyl radical with 1 to 5C atoms, preferably 1 or 2C atoms. If they are in the hydrogenated or partly hydrogenated forms, they can also contain double-bonded oxygen (ketofunctions). In the case of nitrogen-heterocyclic radicals which contain an =NH group in the ring, bonding to the alkyl, alkoxy, alkylamino, dialkylamino, alkylmercapto, alkylsulphoxy or alkylsulphonyl group $R^3$ or $R^4$ can also be via the N atom of this =NH group. If the nitrogen-heterocyclic radicals containing a keto function form tautomeric forms, they can also be in this form.

Examples of preferred heterocyclic radicals are pyrrole, pyrroline, pyrrolidine, pyrrolidone, imidazol-1-yl, imidazol-4-yl, 2-methyl-imidazol-4-yl, oxazole, oxazoline, oxazolidine, oxazolidone, in particular 2-oxazolidon-5-yl, oxadiazol-2-yl, 5-methyl-oxadiazol-2-yl, pyrid-2-, -3- or -4-yl; 2-hydroxy-4-methylpyrid-6-yl or 2-pyridone-4-methyl-6-yl, 2-pyron-4-, -5- or -6-yl and 2-pyrone-4-methyl-6-yl.

Heterocycloalkylcarbonyl radicals $R^{10}$ of the above formula arre derived from carboxylic acids of the formula

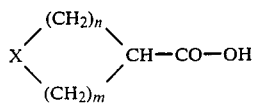

such as, for example, from pyrrolidine-2-carboxylic acid, pyrrolidine-2-carboxylic acid which is substituted in the 1-position by $R^8$, pyrrolid-2-one-5-carboxylic acid, the derivative thereof substituted in the 1-position by $R^8$, pyridine-2-, -3- or -4-carboxylic acid, piperidine-2-, -3- or -4-carboxylic acid or the derivative thereof substituted in the 1-position by $R^8$, furan-2- or -3-carboxylic acid or thiophene-2- or -3-carboxylic acid.

Examples of radicals of the above formula

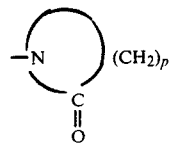

are pyrrolid-2-on-1-yl, piperid-2-on-1-yl and the caprolactam radical

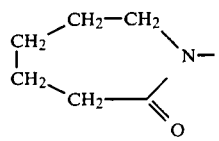

Examples of radicals of the following formula already mentioned above

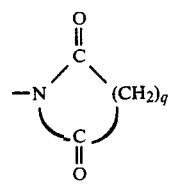

are: the succinimide radical

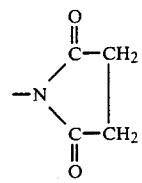

the glutarimide radical

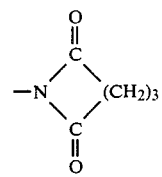

th pyrotartaric acid imide radical

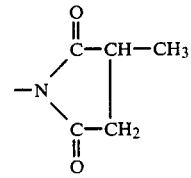

the symmetric dimethylsuccinic acid imide radical and the pimelic acid imide radical.

Examples of radicals of the formulae

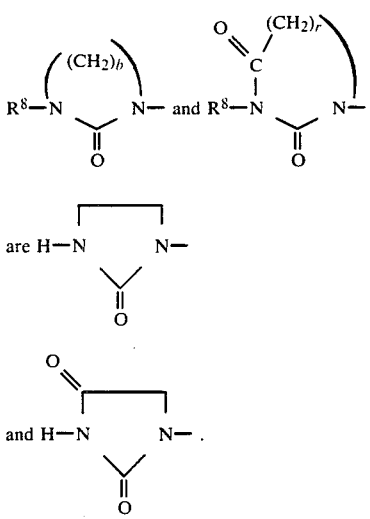

If $R^{11}$ is hydrogen, the following meanings are preferred for $R^{10}$: 1-formyl-pyrrolidine-2-carbonyl, pyrrolidine-2-carbonyl, 1-acetyl-pyrrolidine-2-carbonyl, 5-oxo-pyrrolidine-2-carbonyl, 2-furylcarbonyl, 2,3,4-pyridylcarbonyl, 2-thienylcarbonyl, benzoyl, o-, m- or p-methylbenzoyl, o-, m- or p-methoxybenzoyl, 3,4-dimethoxybenzoyl, o-, m- or p-chlorobenzoyl, o-, m- or p-cyanobenzoyl, o-, m- or p-nitrobenzoyl, 4-chlorophenoxyacetyl, chloroacetyl, dichloroacetyl and aminoacetyl.

If $R^{11}$ is not hydrogen, the following $R^{10}/R^{11}$ combinations are preferred: acetyl/acetyl, acetyl/alkyl($C_1$–$C_3$), chloroacetyl/alkyl($C_1$–$C_3$) and alkyl($C_1$–$C_5$)/alkyl($C_1$–$C_5$), in particular acetyl/methyl; acetyl/ethyl; chloroacetyl/methyl; chloroacetyl/ethyl; methyl/methyl and ethyl/ethyl.

If $R^{10}$ and $R^{11}$ together form a divalent radical bonded to the N atom, this is preferably butylene-1-carbonyl, pentylene-1-carbonyl, butylene-1,4-dicarbonyl, butenylene-1,4-dicarbonyl, phenylene-1,2-dicarbonyl, phenylene-1-sulphonyl-2-carbonyl, phenylene-1-sulphinyl-2-carbonyl, phenylene-1-sulphenyl-2-carbonyl or pyridyl-2,3-dicarbonyl.

The same rules and preference conditions as have been stated above for the radicals $R^3$ to $R^5$ apply to the position and combination of the substituents $R^{12}$ to $R^{14}$ of a phenoxy radical

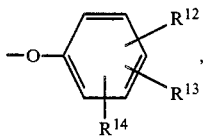

which is the substituent of an alkanoyl group $R^{10}$, and of a benzoyl radical $R^{10}$ of the formula

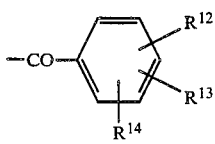

Preferred phenyl radicals R are those in which $R^4$ and $R^5$ denote hydrogen and $R^3$ has one of the following meanings: o-, m- or p-nitro, o-, m- or p-cyano, o-, m- or p-alkoxycarbonyl, 2-, 3- or 4-pyridylmethyl, 5-methyl-(1,3,4-oxdiazol)-2-yl-methoxy, 2-, 3- or 4-pyridylmethoxy, (4-methyl-2-pyron-6-yl)-methoxy, (4-methyl-2-pyridon-6-yl)-methoxy, (2-methyl-imidazol-4(5)-yl)-methoxy, 2-(1-imidazolyl)-ethoxy, (oxazolidin-2-on)-5-yl-methoxy, 2-(methoxy)-ethoxy or 2-(dimethylamino)-ethoxy. Those radicals R in which $R^3/R^4/R^5$ are in one of the following combinations are also preferred: alkyl/H/H; fluorine, chlorine or bromine/H/H; alkoxy/H/H; alkyl/alkyl/H; alkyl/alkoxy/H; alkoxy/alkoxy/H; alkoxy/alkoxy/alkoxy; monoalkylamino/H/H; dialkylamino/H/H and acetylamino/H/H, and those radicals R in which $R^3$ is an alkyl or, in particular, alkoxy group substituted as described above, $R^4$ is hydrogen or alkyl or alkoxy of the abovementioned chain length, in particular methyl or methoxy, and $R^5$ is hydrogen are also preferred.

Examples of such preferred radicals R are methylphenyl, in particular 4-methylphenyl, methoxyphenyl, in particular 4-methoxyphenyl, chlorophenyl, in particular 4-chlorophenyl, dimethoxyphenyl, in particular 3,4-dimethoxyphenyl, trimethoxyphenyl, in particular 3,4,5-trimethoxyphenyl, dimethylaminophenyl, in particular 4-dimethylaminophenyl, and 4-acetylaminophenyl.

Other preferred radicals R are: 2-thienyl, 3-pyridyl, 2-furyl, 2-pyrrolyl, 3-indolyl and 4-(5-amino-1,3-dimethyl-pyrazolyl).

An alkyl radical $R^1$ can be straight-chain or branched and as a rule has 1 to 5 C atoms.

Preferred alkyl radicals $R^1$ are straight-chain and have 1 to 5, in particular 1 or 2, C atoms. An aralkyl radical $R^1$ is preferably a phenalkyl radical which contains 1 to 3, in particular 1 or 2, C atoms in the alkyl bridge. The phenyl nucleus of a phenalkyl radical $R^1$ is unsubstituted, but can also preferably carry one or two substituents. Possible substituents here are: halogen, in particular fluorine, chlorine, or bromine, alkyl with 1 to 5, preferably 1 or 2, C atoms, alkoxy with 1 to 5, preferably 1 or 2, C atoms, the amino group, monoalkylamino with 1 to 5, preferably 1 or 2, C atoms and dialkylamino with a total of 2 to 6, preferably 2 to 4, C atoms.

The substituents of the phenyl nucleus of a phenylalkyl radical $R^1$ can be in any desired position. An individual substituent can be in the 2-, 3- or 4-position of the phenyl nucleus.

In the case of disubstitution, the substituents can be in the 2,3-; 3,2-; 2,4-; 4,2-; 2,5-; 5,2; 2,6-; 3,4-; 4,3- or 3,5-position. A phenalkyl radical which is disubstituted in the phenyl nucleus preferably has only one optionally substituted amino group. Any second substituent present is preferably chlorine, an alkyl radical, in particular methyl, or an alkoxy radical, in particular methoxy.

If $R^1$ represents an alkanoyl radical of the formula —CO—$R^9$, the alkyl radical $R^9$ can likewise be straight-chain or branched. As a rule, this alkyl radical has 1 to 5, in particular 1 or 2, C atoms.

If $R^1$ represents an acyl radical of the formula —CO—$R^9$ and $R^9$ represents pyridyl, the pyridyl radical can be bonded in the 2-, 3- or 4-position.

A phenoxy radical which is bonded as the substituent of an alkyl group $R^9$ can be unsubstituted or substituted by halogen, preferably chlorine, alkyl with 1 to 4 C atoms, preferably methyl, or alkoxy with 1 to 4 C atoms, preferably methoxy. Particularly preferred compounds according to the invention are those in which $R^1$ represents hydrogen; alkyl with 1 or 2C atoms, in particular methyl; alkanoyl with 1 to 3C atoms, in particular acetyl; or benzoyl or nicotinoyl.

An alkyl radical $R^2$ can be straight-chain or branched and as a rule has 1 to 5C atoms. Basic groups by which an alkyl group $R^2$ can optionally be substituted correspond to the formula

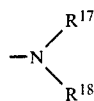

wherein $R^{17}$ and $R^{18}$ independently of one another denote hydrogen; alkyl with 1 to 6C atoms; or cycloalkyl with 3 to 6C atoms, or wherein $R^{17}$ and $R^{18}$ together repreent a polymethylene chain with 2 to 5C atoms, which can optionally be interrupted by an oxygen or sulphur atom or by a group $=N-R^{19}$, wherein $R^{19}$ denotes hydrogen; alkyl with 1 to 4C atoms, preferably methyl; or phenalkyl with 1 to 3C atoms in the alkyl bridge, preferably benzyl.

A phenyl radical $R^2$ can be unsubstituted or can carry up to three, preferably two, and in particular one, of the following substituents: halogen, alkyl with 1 to 5C atoms; —OH; alkoxy with 1 to 5C atoms; alkanoyloxy with 1 to 5C atoms; benzoyloxy; alkylmercapto with 1 to 5C atoms; —NH₂; monoalkylamino with 1 to 5C atoms; dialkylamino with a total of 2 to 5C atoms; and alkanoylamino with 1 to 4C atoms, it being possible for the alkyl radical with 1 to 5C atoms to be in turn substituted by —NH₂; monoalkylamino with 1 to 5C atoms; dialkylamino with a total of 2 to 5C atoms; or alkanoylamino with 1 to 4C atoms.

The same preference rules which have been stated above in respect of the substitution of a phenyl radical R otherwise apply to the number and position of these substituents.

Particularly preferred tetrahydropyridazinone derivatives according to the invention are those in which several of the abovementioned preferred features are combined.

Preferred tetrahydropyridazinones according to the invention are also those in which $R^1$ is hydrogen, and furthermore those in which $R^2$ is hydrogen, and, in particular, those in which $R^1$ and $R^2$ are hydrogen. Apart from their good pharmaceutical activity, these groups of compounds according to the invention can also be used as intermediates for further reaction with alkylating agents or acylating agents to give compounds according to the invention in which $R^1$ and/or $R^2$ have meanings other than hydrogen.

All the inorganic and organic acids of sufficient strength to protonate the compounds according to the invention are in principle suitable for salt formation. The choice can thus be made in a manner which is known per se. Examples of suitable acids are HCl, HBr, H₂SO₄, phosphoric acid, formic acid, acetic acid, propionic acid, lactic acid, oxalic acid, fumaric acid, tartaric acid, benzoic acid, salicyclic acid and methanesulphonic acid.

Preferred salts of compounds according to the invention are those which are derived from pharmacologically acceptable acids.

The tetrahydropyridazinone derivatives according to the invention and their salts have useful pharmacological actions.

The tetrahydropyridazinone derivatives according to the invention are prepared by reacting acyl-γ-butyrolactones of the formula II with hydrazine or hydrazine derivatives of the formula III according to the equation

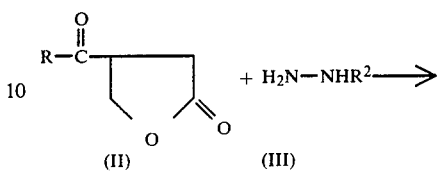

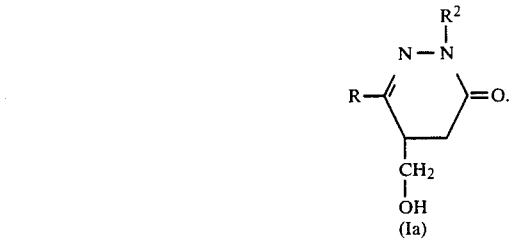

wherein R and $R^2$ have the abovementioned meanings and, if compounds according to the invention in which $R^1$ is other than hydrogen are to be prepared, subsequently etherifying or esterifying the hydroxymethyl group in the 5-position with an etherifying or esterifying agent of the formula IV $$R^1-X \qquad (IV)$$

wherein $R^1$ has the abovementioned meaning and X is a radical which can be split off as an anion.

The abovementioned compounds of the formula Ia according to the invention can also be prepared in two independent steps, by first reacting the butyrolactone derivative II with hydrazine (NH₂—NH₂) to give the tetrahydropyridazinone derivative Ib according to the invention

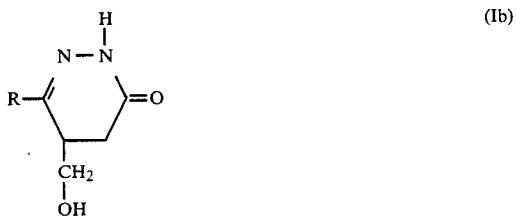

which, if desired, can be alkylated in the 2-position in a manner which is known per se. This process is advantageous if corresponding substituted hydrazines of the formula III are less easily accessible.

The first reaction step in the preparation of the tetrahydropyridazinone derivatives according to the invention, that is to say the reaction of the acyl-γ-butyrolactones of the formula II with hydrazines of the formula III, comprises the reaction of a γ-ketocarboxylic acid or of a γ-ketocarboxylic acid derivative with hydrazine, with cyclisation to the corresponding tetrahydropyridazinone derivative. This reaction and the reaction conditions have been known per se for a long time. Thus, the reaction of levulinic acid (γ-ketovaleric acid) with phenylhydrazine to give 2-phenyl-5-methyl-tetrahydropyridazin-3-one has already been reported by E. Fischer in "Liebigs Annalen der Chemie", Volume 236, page 147 in 1886. Further statements on this reaction are to be found in Liebigs Annalen der Chemie, Volume 724, pages 217-220 (1969).

The reaction is advantageously carried out in the liquid phase, for which the presence of an inert solvent or diluent is as a rule necessary. Water is a suitable solvent in many cases, but organic solvents from the series comprising the alkanols; alkanediols; diglycol or triglycol and ethers and half-ethers thereof; dialkyl ethers; cyclic ethers, such as, for example, tetrahydrofuran or dioxane; strongly polar aprotic solvents, such as, for example, dimethylformamide, dimethylsulphoxide or pyridine; aromatic hydrocarbons, such as benzene, toluene or xylene; and aliphatic or aromatic halogenohydrocarbons, such as methylene chloride, chloroform, trichloroethylene, monochlorobenzene and dichlorobenzene, are used in particular.

The reaction can in principle be carried out at temperatures between room temperature and the boiling point of the particular solvent used. In the case of low-boiling solvents, the reaction can also be carried out in a closed system under pressure at a temperature above the boiling point of the solvent, in order to accelerate the cyclisation. As a rule, the reaction is not carried out above 200° C. A reaction temperature of between 50° and 100° C. is preferably used. The reaction can also be accelerated by acid catalysis. If the reaction is carried out at a low temperature, the hydrazones intermediately formed, of the formula IIa, can be isolated, if appropriate as hydrates,

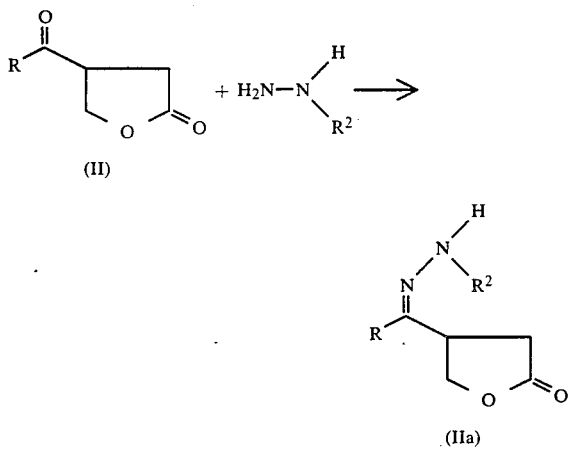

and can then be converted into the tetrahydropyridazinones of the formula Ia by warming, if necessary under acid catalysis, as described above.

The compounds of the formula Ia according to the invention obtained in the first reaction step have a hydroxymethyl group in the 5-position of the tetrahydropyridazinone system, which, if desired, can be etherified or esterified in a seciond reaction step. An enormous number of etherifications or esterifications of OH groups bonded to aliphatic radicals have already been described, and the conditions of these reactions are thus very well known. A good review of the reaction conditions and reagents advantageous for these reactions is to be found, for example, in Houben Weyl Volume 6/3, page 22 et seq. and Houben Weyl Volume 8, page 516 et seq.; Synthesis (1982) page 833; and J. Med. chem. Volume 25, page 620 (1982).

In the context of the present invention, any desired etherification of the hydroxymethyl group in the 5-position can be carried out by warming the compound of the formula Ia with an alkylating agent of the formula IV. In the alkylating agent of the formula $R^1X$, X denotes a radical which can be split off as an anion. A large number of such radicals are likewise known from the literature.

Examples of these radicals are halogen atoms, an alkylsulphato group or, for example, arylsulphonyloxy. Depending on the nature of the radical X, it is advantageous to promote the advance of the reaction by addition of a suitable catalyst or of a base.

Examples of suitable bases are tertiary amines, but preferably inorganic bases, such as alkali metal hydroxides, or salts of alkali metals with weak inorganic or organic acids, in particular, for example, the carbonates of the alkali metals. The alkylation reaction is also advantageously carried out in a solvent, preferably in an organic solvent, or in an excess of the alkylating agent. Examples of possible solvents for the alkylation are ethers, in particular cyclic ethers, such as tetrahydrofuran or dioxane, and aromatic hydrocarbons, such as, for example, benzene, toluene or xylene.

Any desired esterification of the hydroxymethyl group in the 5-position can likewise be carried out in a manner which is known per se. The carboxylic acid imidazolides can be particularly advantageously employed as the esterifying agent of the formula $R^1X$.

Other suitable esterifying agents are those in which X represents, for example, the alkanoyloxy radical. In this case, carboxylic acid anhydrides are used. The esterification reaction can in principle be carried out without any solvent, but it is advantageous, especially if reactive esterifying agents are used, to employ a solvent or diluent to moderate the reaction. All the organic solvents which cannot react with the acylating agents are suitable. Aromatic hydrocarbons, such as benzene, toluene and xylene, are chiefly used as solvents, diluents or dispersing agents, and it is advantageous, especially if the free bases are to be prepared and not the salts of tetrahydropyridazinones according to the invention, likewise to carry out the acylation in the presence of a basic acid-trapping agent, such as, for example, a tertiary organic amine base. Acylations of the type mentioned can also be carried out in the presence of pyridine or pyridine derivatives as the solvent. In this case, the solvent itself acts as the acid-trapping agent. The acylation of the compounds of the formula Ia according to the invention can also be carried out at temperatures between normal room temperature and temperatures up to 150° C. Higher temperatures as a rule provide no advantages. It is particularly advantageous to carry out the acylation in the region below the boiling point of the solvent or dispersing agent used, in particular at temperatures between room temperature and 60° C.

According to the equation given above, the radical $R^2$ is introduced into the compounds according to the invention by using a hydrazine substituted by $R^2$ for reaction with the ketocarboxylic acid derivative. However, as already stated above, it is also possible subsequently to introduce the radical $R^2$ into a compound of the formula Ib according to the invention. The introduction of a radical $R^2$ into the 2-position of compounds of the formula Ib according to the invention is alkylation or arylation using an alkylating or arylating agent of the formula V $$R^2X \qquad (V)$$

N-alkylations on heterocyclic compounds have likewise been known in the prior art for a long time and have been described in detail in numerous publications, such as, for example, Heterocyclic Compounds Volume 28, page 37 et seq. (1973). In the alkylating agent $R^2X$, X also denotes a radical which can be split off as an anion, preferably a halogen atom, an alkylsulphato group or arylsulphonyloxy. It is advantageous to promote the advance of the reaction by addition of a suitable catalyst or a base which collects the radical X split off as an anion. Examples of suitable bases are tertiary amines and, preferably, inorganic bases, such as alkali metal hydroxides, or salts of alkali metals with weak inorganic or organic acids, in particular, for example, the carbonates of the alkali metals. This alkylation reaction is also advantageously carried out in a solvent, for example in water, or in an organic solvent. Examples of possible solvents for the alkylation are ethers, in particular cyclic ethers, such as tetrahydrofuran or dioxane, and aromatic hydrocarbons, such as, for example, benzene, toluene or xylene.

Acyl-γ-butyrolactones of the formula II wherein R denotes one of the radicals of the formulae

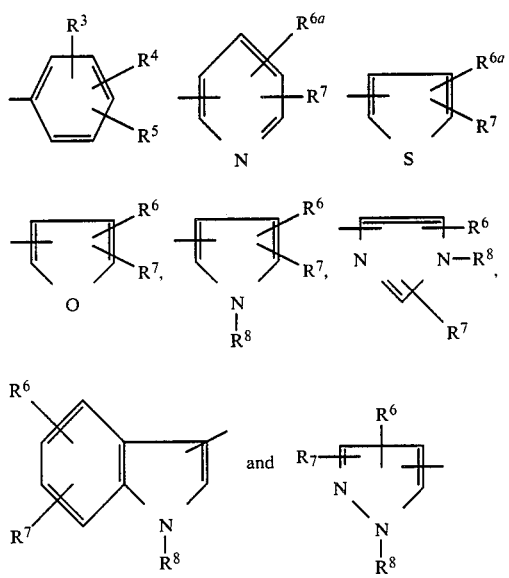

$R^3$, $R^4$ and $R^5$ independently of one another denote iodine; alkyl with 3 to 5C atoms; —OH; alkoxy with 2 to 5C atoms; alkanoyloxy with 1 to 5C atoms; benzoyloxy; alkylmercapto with 1 to 5 C atoms; —NH$_2$; monoalkylamino with 1 to 5C atoms; dialkylamino with a total of 2 to 5C atoms; or alkanoylamino with 1 to 4C atoms; and $R^4$ and $R^5$ additionally also denote hydrogen; one of the radicals $R^3$, $R^4$ or $R^5$ denotes o- or m-methoxy, o- or m-methyl or -ethyl, o- or m-bromo, o-fluoro or o-chloro, and the other two denote hydrogen; two of the radicals $R^3$, $R^4$ and $R^5$ denote 2,3-, 2,4-, 2,5-, 2,6- or 3,5-dimethoxy, -dichloro or -difluoro or 3,4-difluoro and the third denotes hydrogen, or all three of the radicals $R^3$, $R^4$ and $R^5$ denote 2,3,4-; 2,3,5-; 2,3,6-; 2,4,5- or 2,4,6-trimethoxy; and $R^3$ and $R^4$ also denote nitro; cyano; or alkylmercapto, alkylsulphoxy or alkylsulphonyl with in each case 1 to 5C atoms, alkyl(-$C_1$-$C_5$)-oxycarbonyl or a group of the formula —NR$^{10}$R$^{11}$, it being possible for the alkyl, alkoxy, alkylamino, dialkylamino, alkylmercapto, alkylsulphoxy and alkylsulphonyl radicals $R^3$ and $R^4$ to be further substituted in the alkyl part by hydroxyl, alkoxy with 1 to 5, preferably 1 or 2,C atoms, carboxyl, alkoxycarbonyl with a total of 2 to 7C atoms or aminocarbonyl of the formula

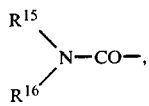

wherein $R^{15}$ and $R^{16}$ independently of one another denote hydrogen or alkyl with 1 to 5C atoms, which can in turn be substituted by alkoxy with 1 to 4C atoms, halogen, in particular chlorine or bromine, —NH$_2$ or mono- or di-alkylamino with 1 to 4C atoms in the alkyl groups, or wherein $R^{15}$ and $R^{16}$, together with the N atom to which they are bonded, form the radial of a 5-membered or 6-membered heterocyclic ring which optionally contains a further hetero-atom, such as, for example, pyrrolidine, piperidine, piperazine, alkylpiperazine, morpholine or thiomorpholine, or by amino, monoalkylamino with 1 to 5, preferably 1 or 2,C atoms, dialkylamino with a total of 2 to 6C atoms or a 5-membered or 6-membered heterocyclic radical with 1 to 3 hetero-atoms; and $R^4$ and $R^5$ additionally also denote hydrogen; $R^6$ and $R^7$ independently of one another denote hydrogen; halogen, in particular chlorine and bromine; amino, monoalkylamino with 1 to 5C atoms, dialkylamino with a total of 2 to 6C atoms, hydroxyl, alkoxy with 1 to 5C atoms or alkyl with 1 to 5C atoms; $R^{6a}$ and $R^7$ independently of one another denote halogen, in particular chlorine and bromine; amino, monoalkylamino with 1 to 5C atoms, dialkylamino with a total of 2-6 C atoms, hydroxyl, alkoxy with 1 to 5C atoms or alkyl with 1 to 5C atoms; or, if pyridyl is bonded in the 2- or 4-position and thienyl in the 3-position, also hydrogen, $R^8$ denotes hydrogen, alkyl with 1 to 5C atoms, alkanoyl with 1 to 5C atoms or a radical of the formula

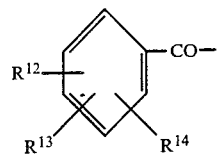

$R^9$ denotes alkyl with 1 to 5C atoms, which is optionally substituted by an optionally substituted phenoxy radical,

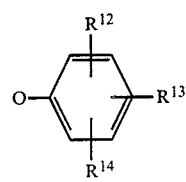

a group of the formula

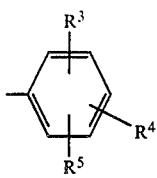

or pyridyl; $R^{10}$ denotes alkanoyl with 1 to 5C atoms, which can optionally be substituted by —OH, —NH$_2$, halogen, in particular chlorine or bromine, alkoxy with 1 to 5C atoms or phenoxy of the formula

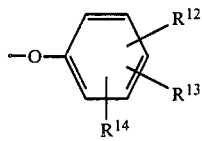

benzoyl of the formula

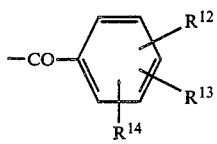

heterocycloalkylcarbonyl of the formula

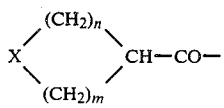

wherein n=2; 3 or 4, m=0; 1 or 2, and, preferably, n+m=3 or 4, and X represents oxygen, sulphur or a group of the formula =N—$R^8$, it being possible for the heterocyclic nucleus to be further substituted by alkyl with 1 to 5, preferably 1 or 2, C atoms, chlorine, bromine or double-bonded oxygen (=O), or $R^{10}$ denotes

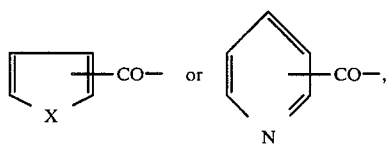

and $R^{11}$ denotes hydrogen, alkyl with 1 to 5C atoms or alkanoyl with 1 to 5C atoms, or $R^{10}$ and $R^{11}$, together with the nitrogen atom to which they are bonded, form a pyrrolidine, piperidine, piperazine, morpholine or thiomorpholine ring or a ring of the formula

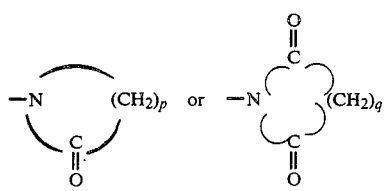

wherein p=3, 4 or 5; and q=2 or 3, or

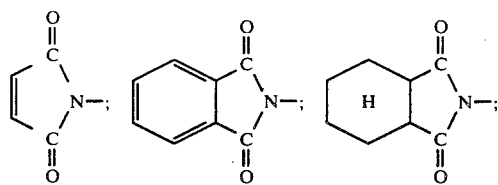

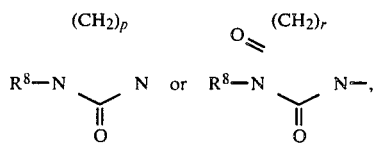

wherein r=1 or 2, or

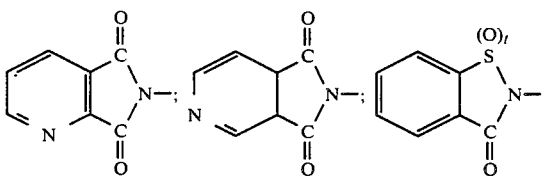

or

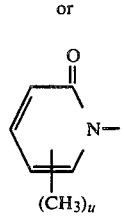

wherein u=0, 1 or 2 and t=0, 1 or 2, which can optionally be further substituted by alkyl with 1 to 5, preferably 1 or 2, C atoms, and $R^{12}$ to $R^{14}$ denote hydrogen, alkyl with 1 to 5C atoms alkoxy with 1 to 5C atoms, nitro, cyano, halogen, in particular chlorine or bromine, amino, monoalkylamino with 1 to 5C atoms, dialkylamino with a total of 2 to 6C atoms, alkanoylamino with 1 to 5C atoms or benzoylamino, have not hitherto been described and are thus, as intermediates for the preparation of the tetrahydropyridazinones of the formula I according to the invention, likewise the subject of the invention.

The acyl-γ-butyrolactones of the formula II used as starting materials for the preparation of tetrahydropyridazinone derivatives according to the invention can be prepared from 4-ketobutyric acids, substituted in the 4-position, of the formula VI by reaction with formaldehyde:

(VI)

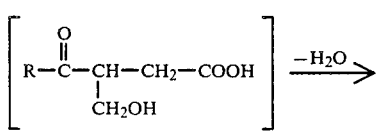

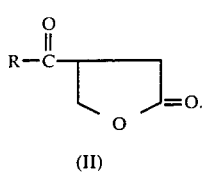

(II)

R has the same meanings in the formulae II and VI. Oxymethylations of CH-acid compounds by reaction with formaldehyde are likewise already the prior art (in this context, compare J. Org. Chem. 24, pages 586–89 (1959); and Synthesis (1980) pages 825–828).

The reaction can be carried out with or without a solvent, using aqueous formaldehyde, paraformaldehyde or a formaldehyde dissolved in an organic solvent. The reaction is as a rule carried out in the presence of a weakly basic catalyst, such as, for example, ammonium acetate or piperidine acetate. If the reaction is carried out in an aqueous medium, hydroxides or basic salts of alkali metals or alkaline earth metals are advantageously used as the basic catalysts. The hydroxymethylation as a rule already proceeds at a considerable rate at room temperature. The reaction can therefore be carried out at temperatures between 20° and 100° C. When the hydroxymethylation has been carried out, the reaction mixture is acidified and is subsequently stirred at temperatures between 20° and 120° C., preferably at room temperature, for some hours. Cyclisation of the hydroxymethyl-γ-ketobutyric acid formed to the butyrolactone derivative of the formula II thereby occurs.

In principle, it is also possible to isolate the hydroxymethyl-γ-ketobutyric acid in the free, open-chain form after the acidification and to react it with hydrazine or a hydrazine derivative $R^2$—NH—$NH_2$ to give the tetrahydropyridazinone derivatives according to the invention (compare E. Fischer, Liebigs Annalen der Chemie).

γ-Ketobutyric acid derivatives of the formula VI which are used for the preparation of the acyl-γ-butyrolactones of the formula II can be obtained in various known ways. Independently of the nature of the radical R, addition of aldehydes of the formula R—CHO onto acrylic acid or acrylic acid derivatives, in particular acrylic acid esters, leads to good yields of the desired γ-keto-butyric acids or -butyric acid derivatives. This addition reaction was described in 1976 by H. Stetter in "Angewandte Chemie", Issue 21, page 695 et seq. The reaction is catalysed by the same catalysts which are suitable for the known benzoin condensation. Cyanide ions and quaternary thiazolium salts are particularly suitable for this purpose. Suitable solvents for carrying out these addition reactions are polar solvents, and lower alkanols, such as methanol or ethanol, and dimethylformamide have proved particularly suitable. The addition reaction already achieves a considerable rate at room temperature, and this rate can be increased further by warming. The reaction is advantageously carried out between room temperature and 60° C., preferably between 30° and 50° C. Examples of aldehydes which can be reacted with acrylic acid or acrylic acid derivatives, in particular acrylic acid esters, in the manner described are benzaldehyde, 2-, 3- or 4-chlorobenzaldehyde, 2,4- or 3,4-dichlorobenzaldehyde, 4-bromobenzaldehyde, 2-, 3- or 4-methyl- or -ethylbenzaldehyde; 4-isopropyl-benzaldehyde, 2-, 3- or 4-hydroxybenzaldehyde, 2,4-dihydroxybenzaldehyde, 2-, 3- or 4-methoxy- or -ethoxy-benzaldehyde, 2,4-, 3,4- or 3,5-dimethoxybenzaldehyde, 3,4,5-trimethoxybenzaldehyde, p-acetoxybenzaldehyde, p-benzyloxybenzaldehyde, 2-, 3- or 4-methylmercaptobenzaldehyde, 2-, or 3- or 4-amino-, -monomethylamino- or -dimethylaminobenzaldehyde, 2-, 3- or 4-nitrobenzaldehyde, 3-methyl-, 3-ethyl- or 3-butyl-pyridine-2-aldehyde, 4-, 5- or 6-methylpyridine-2-aldehyde, 4-chloropyridine-2-aldehyde, 5-nitropyridine-2-aldehyde, 4-chloro-6-methylpyridine-2-aldehyde, 4,6-dichloropyridine-2-aldehyde, 4,6-dimethylpyridine-2-aldehyde, 6-methyl-4-nitropyridine-2-aldehyde, 5-bromo- or 5-chloro-pyridine-3-aldehyde, 2- or 6-methylpyridine-3-aldehyde, 5,6-dichloropyridine-3-aldehyde, 2-methylpyridine-4-aldehyde, 3-ethylpyridine-4-aldehyde, 2-methyl-5-ethylpyridine-4-aldehyde, 2,6-dichloropyridine-4-aldehyde, 2,6-dimethylpyridine-4-aldehyde, 3-nitropyridine-4-aldehyde, 5-chloro- or 5-bromothiophene-2-aldehyde, 3- or 4-bromothiophene-2-aldehyde, 4,5-dichloro- or 4,5-dibromo-thiophene-2-aldehyde, 4- or 5-nitrothiophene-2-aldehyde, 3-bromo-4-nitrothiophene-2-aldehyde, 5-methyl-, -ethyl-, -butyl- or -isobutyl-thiophene-2-aldehyde, 3-methyl-5-nitrothiophene-2-aldehyde, 2-chloro-, 2-bromo- or 2-nitrothiophene-3-aldehyde, 2,5-dichlorothiophene-3-aldehyde, 2,5-dimethyl- or 2,5-diethyl-thiophene-3-aldehyde, 2-butyl-5-methylthiophene-3-aldehyde and 5-tert.-butyl-2-methylthiophene-3-aldehyde.

If R is a substituted phenyl or heteroaryl radical, the γ-ketobutyric acid derivatives of the formula VI can also be obtained by acylating correspondingly substituted benzene derivatives or heterocyclic compounds with succinic anhydride or a succinic acid ester-chloride under Friedel-Crafts conditions. Friedel-Crafts reactions with succinic anhydrides have likewise been the prior art for a long time and have been described in detail in numerous publications, for example in J. Am. Chem. Soc. 70, page 3197 (1948); Liebigs Annalen d. Chemie, 462, page 148 (1928); and U.S. Pat. No. 2,447,998.

In the Friedel-Crafts acylation, the reactants are reacted with one another in an inert solvent, preferably an inert aromatic hydrocarbon, or in carbon disulphide, in the presence of a Friedel-Crafts catalyst at temperatures between room temperature and the boiling point of the solvent. If carbon disulphide is used as the solvent, adequate cooling must be ensured, so that the solvent does not evaporate. If nitrobenzene, which is a particularly suitable solvent for carrying out Friedel-Crafts reactions, is used, the temperature should not exceed 50° C., as is known, since vigorous reactions may otherwise occur. If γ-ketobutyric acids of the formula VI in which R is, for example, chlorophenyl, alkylphenyl or dialkylphenyl are to be prepared, succinic anhydride can be reacted in a simple manner with a Friedel-Crafts catalyst in the correspondingly substituted benzene derivative, which is used in a relatively large excess and hence at the same time acts as the solvent. As is known, Lewis acids, such as $AlCl_3$, $SbCl_5$, $BF_3$ or $ZnCl_2$, or proton acids, such as, for example, HF, $H_2SO_4$, $H_3PO_4$ or $P_2O_5$, are as a rule used as the Friedel-Crafts catalyst. The reaction is preferably carried out with aluminium chloride as the Friedel-Crafts catalyst.

The acid addition salts of the tetrahydropyridazinones according to the invention are prepared in a known manner by simply combining the compound according to the invention with the desired acid. Advantageously, for preparation of acid addition salts of the compounds of the formula I, the latter are dissolved in an organic solvent and a solution of the desired acid is added. Thus, for example, the hydrochlorides of the pyridazinones of the formula I according to the invention are obtained by dissolving the compounds in alcohol and adding an equivalent amount of a solution of hydrogen chloride in ether to the alcoholic solution.

The tetrahydropyridazinone derivatives of the formula I according to the invention wherein R is a phenyl radical substituted according to the above definition or an unsubstituted or substituted heterocyclic radical, and tetrahydropyridazinones of the formula I in which R is an unsubstituted phenyl radical, and their physiologically acceptable salts exhibit pronounced anti-thrombotic, platelet aggregation-inhibiting, antianginal, cardiotonic hypotensive actions. Surprisingly, they are considerably superior to the hitherto known compounds of the same type of action and are therefore outstandingly suitable for the treatment of diseases of the heart and of the vascular system. They exhibit an excellent activity in various tests, such as, for example, platelet aggregation in accordance with the method of Born, Nature 194, page 927, (1961); arachidonic acid lethality in rabbits, Science 193, page 1085, (1974); and prevention of arterial and venous thrombosis in rabbits, and exhibit an advantageous haemodynamic profile after peroral administration to conscious dogs. Studies using the tests mentioned and a number of other tests show that, surprisingly, the compounds which can be prepared according to the invention have a particularly advantageous action profile, which does not exist in this form in known products, coupled with a low toxicity.

The tetrahydropyridazinone derivatives of the formula I according to the invention in which R is a phenyl radical which is substituted according to the above definition or an optionally substituted heterocyclic radical, and tetrahydropyridazinones of the formula I wherein R is unsubstituted phenyl can therefore be administered, by themselves or as mixtures with one another, preferably in the form of pharmaceutical formulations, to humans and in this respect are all the subject of the invention.

The pharmaceutical formulations according to the invention contain, as the active constituent, an effective dose of at least one tetrahydropyridazinone derivative according to the invention or of an acid addition salt thereof.

The dosage of the tetrahydropyridazinone derivatives according to the invention is in general between 0.1 and 1000 mg, preferably 1 and 100 mg, per day and is adapted in a known manner to the requirements of the individual case.

Depending on the type of administration, the dose varies within the above dosage range in order to take into consideration, in a known manner, the different absorption conditions.

Thus, in the case of intravenous administration, a dosage in the lower part of the given dosage range is chosen, whilst a dosage more in the upper part of the given dosage range is chosen for oral administration. The daily dose is usually administered in several, for example 2, part doses, the individual dose as a rule being 0.01 to 10 mg per kg of body weight.

The pharmaceutical formulations as a rule contain 0.05 to 100 mg, preferably 1 to 50 mg, per unit of one or more tetrahydropyridazinone derivatives according to the invention or of pharmacologically acceptable salts thereof, in addition to customary, pharmaceutically acceptable excipients or additives.

Examples of suitable excipients are water, vegetable oils, starch, gelatine, lactose, magnesium stearate, waxes, petroleum jelly and the like. Additives which can be used are, for example, wetting agents, disintegrating agents, preservatives and the like.

The pharmaceutical products can be in the form of, for example, tablets, capsules, aqueous or oily solutions or suspensions, emulsions, injectable aqueous or oily solutions or suspensions, dispersible powders or aerosol mixtures. Besides the compounds of the general formula I, the pharmaceutical products can also contain one or more other pharmaceutically active substances, for example agents which stimulate blood flow, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, metildigoxin and lanato-glycosides; coronay dilators such as carbochromene, dipyridamol, nifedipine and perhexiline; antianginal compounds, such as isosorbide dinitrate, isosorbide mononitrate, glycerol trinitrate, molsidomine and verapamil; β-blockers, such as propananolol, oxprenolol, atenolol, metoprolol and penbutolol, and oogenetic-metabolic agents, such as pirilinol.

The following embodiment examples illustrate the invention. The reaction conditions and the reducing, alkylating and acylating agents can be varied in the context of the prior art and the patent claims and the tetrahydropyridazinone derivatives employed can be varied in the context of the patent claims.

EXAMPLE 1

6-(3,4-Dimethoxyphenyl)-5-hydroxymethyl-2,3,4,5-tetrahydro-pyridazin-3-one 15.0 g (0.06 mol) of 4-(3,4-dimethoxyphenyl)-carbonylbutyrolactone and 3.5 g (0.07 mol) of hydrazine hydrate are heated under reflux in 200 ml of ethanol for 10 hours. After the mixture has been cooled, the precipitated product is filtered off with suction, washed and dried.

Yield: 11.6 g, melting point: 203°–205° C. Elemental analysis: ($C_{13}H_{16}N_2O_4$); calculated (%): C 59.1, H 6.1, N 10.6, O 24.2; found (%): C 59.0, H 6.1, N 10.5, O 24.3.

The 4-(3,4-dimethoxyphenyl)-carbonyl-γ-butyrolactone used above as the starting material can be prepared as follows:

23.8 g (0.1 mol) of 4-(3,4-dimethoxyphenyl)-4-oxo-butyric acid are dissolved in 220 ml of 2% strength sodium hydroxide solution, 8.5 g of 39% strength formaldehyde solution are then added and the mixture is stirred at 50° C. for 3 hours. After acidification with hydrochloric acid, the mixture is stirred overnight at room temperature, the semi-solid product is filtered off with suction and taken up in ethyl acetate and the mixture is washed with sodium bicarbonate, dried and concentrated.

Yield: 5.6 g, melting point: 114°–116° C. Elemental analysis: calculated (%): C 62.4, H 5.6, O 32.0; found (%): C 63.2, H 5.7, O 30.9.

The 4-(3,4-dimethoxyphenyl)-4-oxo-butyric acid required is obtained as follows:

240 g of anhydrous aluminium chloride are dissolved in 800 ml of nitrobenzene, and 88 g (0.88 mol) of succinic anhydride and 128 g (0.93 mol) of veratrole are added. After a reaction time of 24 hours at room temperature, the mixture is poured onto a mixture of ice, water and concentrated hydrochloric acid, the nitrobenzene is removed by steam distillation, the mixture is cooled and the precipitate which has separated out is filtered off with suction.

For purification, the precipitate is dissolved in sodium carbonate solution under the influence of heat, the solution is filtered over charcoal and acidified and the precipitate is filtered off with suction, washed neutral and dried.

Yield: 137 g, melting point: 156°–158° C. Elemental analysis: ($C_{12}H_{14}O_5$); calculated (%): C 60.5, H 5.9, O 33.6; found (%): C 60.5, H 5.8, O 33.4.

EXAMPLE 2

6-(4-Methylphenyl)-5-hydroxymethyl-2,3,4,5-tetrahydropyridazin-3-one 10.2 g (0.05 mol) of 4-(4-methylphenyl)-carbonyl-$\gamma$-butyrolactone and 3.0 ml (0.06 mol) of hydrazine hydrate are heated under reflux in 150 ml of ethanol for 1 hour. The resulting solution is evaporated in vacuo and the residue is taken up in methylene chloride. If necessary, the methylene chloride solution is filtered, and is then stirred vigorously with the same volume of water. The desired product thereby precipitates. It is filtered off with suction, washed with water and dried.

Yield: 7.6 g (70% of theory). Melting point: 177°–178° C. Elemental analysis: ($C_{12}H_{14}N_2O_2$); calculated (%): C 66.0, H 6.5, N 12.8, O 14.7; found (%): C 65.6, H 6.5, N 13.0, O 15.1.

The 4-(4-methylphenyl)-carbonyl-$\gamma$-butyrolactone used in the above example is prepared as follows:

96.1 g (0.5 mol) of 4-(4-methylphenyl)-4-oxo-butyric acid are dissolved in 1100 ml of 0.5N sodium hydroxide solution, 44 ml (0.55 mol) of 39% strength formaldehyde solution are then added dropwise and the mixture is stirred at room temperature for 8 hours. After acidification with 55 ml of concentrated hydrochloric acid, stirring is continued for 12 hours, the mixture is extracted with ether and the ether phase is separated off, washed with sodium bicarbonate solution and concentrated. The residue is recrystallised from ethyl acetate.

Yield: 16.1 g. Melting point: 88°–89° C. Elemental analysis: ($C_{12}H_{12}O_3$); calculated (%): C 70.6, H 5.9, O 23.5; found (%): C 70.4, H 6.0, O 23.6.

EXAMPLE 3

6-(4-Chlorophenyl)-5-hydroxymethyl-2,3,4,5-tetrahydropyridazin-3-one 9.0 g (0.04 mol) of 4-(4-chlorophenyl)-carbonyl-$\gamma$-butyrolactone and 3 ml (0.06 mol) of hydrazine hydrate are heated under reflux in 15 ml of ethanol for 1 hour. The resulting solution is evaporated to dryness and the residue is recrystallised from methanol.

Yield: 3.1 g (32% of theory). Melting point: 170°–172° C. Elemental analysis: ($C_{11}H_{11}ClN_2O_2$); calculated (%): C 55.4, H 4.6, N 11.7, O 13.4, Cl 14.9; found (%): C 55.0, H 4.9, N 11.3, O 12.9, Cl 14.5.

The 4-(4-chlorophenyl)-carbonyl-$\gamma$-butyrolactone used in the above example is prepared as follows:

106.3 g (0.5 mol) of 4-(4-chlorophenyl)-4-oxo-butyric acid, 1100 ml of 0.5N sodium hydroxide solution and 44 ml (0.55 mol) of 39% strength formaldehyde solution are reacted and worked up, as described above.

Yield: 47.6 g. Melting point: 82°–83° C. Elemental analysis: ($C_{11}H_9ClO_3$); calculated (%): C 58.8, H 4.0, Cl 15.8, O 21.4; found (%): C 59.1, H 4.0, Cl 15.3, O 21.8.

EXAMPLE 4

6-(4-Acetylaminophenyl)-5-hydroxymethyl-2,3,4,5-tetrahydro-pyridazin-3-one 9.9 g (0.04 mol) of 4-(4-acetylaminophenyl)-carbonyl-$\gamma$-butyrolactone and 2.5 g (0.05 mol) of hydrazine hydrate are heated under reflux in 150 ml of ethanol for 2 hours and the mixture is worked up as described in Example 3.

Yield: 3.6 g (34% of theory). Melting point: 229°–230° C. Elemental analysis: ($C_{13}H_{15}N_3O_3$); calculated (%): C 59.8, H 5.8, N 16.1, O 18.4; found (%): C 59.6, H 5.8, N 15.6, O 18.9.

The 4-(4-acetyl-aminophenyl)-carbonyl-$\gamma$-butyrolactone used in the above embodiment example is prepared as follows:

94.1 g (0.4 mol) of 4-(4-acetylaminophenyl)-4-oxo-butyric acid, 880 ml of 0.5N sodium hydroxide solution and 35 ml (0.44 mol) of 39% strength formaldehyde solution are used and worked up, as described above.

Yield: 27 g. Melting point: 152°–154° C. Elemental analysis: ($C_{13}H_{13}NO_4$); calculated (%): C 63.2, H 5.3, O 25.9, N 5.7; found (%): C 63.1, H 5.5, O 26.5, N 5.3.

EXAMPLE 5

(6-(3,4-Dimethoxyphenyl)-3-oxo-2,3,4,5-tetrahydro-pyridazin-5-yl)-methyl pyridine-3-carboxylate 1.3 g (0.01 mol) of nicotinic acid and 1.7 g (0.01 mol) of carbonyl diimidazole are heated under reflux in 30 ml of tetrahydrofuran for 15 minutes. After the mixture has been cooled, 2.6 g (0.01 mol) of 6-(3,4-dimethoxyphenyl)-5-hydroxymethyl-2,3,4,5-tetrahydro-pyridazin-3-one are added, with stirring. After a reaction time of 12 hours, the mixture is evaporated, the residue is taken up in methylene chloride, the methylene chloride mixture is washed with sodium bicarbonate solution, dried and evaporated and the residue is recrystallised from methanol.

Yield: 2.5 g (68% of theory). Melting point: 89°–91° C. Elemental analysis: ($C_{19}H_{19}N_3O_5$); calculated (%): C 61.8, H 5.2, N 11.4, O 21.7; found (%): C 60.6, H 5.9, N 10.9, O 22.4.

The following compounds, for example, can be prepared in an analogous manner: 6-(4-dimethylaminophenyl-5-hydroxymethyl-2,3,4,5-tetrahydro-pyridazin-3-one, (6-(3,4-dimethoxyphenyl)-3-oxo-2,3,4,5-tetrahydropyridazin-5-yl)-methyl acetate, (6-(4-chlorophenyl)-3-oxo-2,3,4,5-tetrahydro-pyridazin-5-yl)methyl pyridine-3-carboxylate, 2-(2-dimethylaminoethyl)-5-hydroxymethyl-6-(4-methylphenyl)-2,3,4,5-tetrahydro-pyridazin-3-one, 6-(4-acetoxyphenyl)-5-hydroxymethyl-2,3,4,5-tetrahydro-pyridazin-3-one, 6-(4-bromophenyl)-5-hydroxymethyl-2,3,4,5-tetrahydropyridazin-3-one, 6-(3-aminophenyl)-5-hydroxymethyl-2,3,4,5-tetrahydro-pyridazin-3-one, 5-hydroxymethyl-6-(3-hydroxyphenyl)-2,3,4,5-tetrahydro-pyridazin-3-one, 6-(3,4-dimethoxyphenyl)-5-hydroxymethyl-2-phenyl-2,3,4,5-tetrahydro-pyridazin-3-one, 6-(3-methoxyphenyl)-5-hydroxymethyl-2,3,4,5-tetrahydro-pyridazin-3-one, 5-hydroxymethyl-6-(2-methylphenyl)-2,3,4,5-tetrahydro-pyridazin-3-one,
5-hydroxymethyl-6-(3-pyridyl)-2,3,4,5-tetrahydro-pyridazin-3-one, 6-(2-chlorophenyl)-5-hydroxymethyl-2,3,4,5-tetrahydro-pyridazin-3-one and
5-hydroxymethyl-6-(3,4,5-trimethoxyphenyl)-2,3,4,5-tetrahydropyridazin-3-one.

EXAMPLE 6

(6-(3,4-Dimethoxyphenyl)-3-oxo-2,3,4,5-tetrahydropyridazin-5-yl)-methyl 4-chlorophenoxyacetate 4.7 g (0.025 mol) of 4-chlorophenoxyacetic acid and 4.3 g (0.027 mol) of carbonyldiimidazole are heated under reflux in 100 of tetrahydrofuran for 15 minutes. After the mixture has been cooled, 6.7 g (0.025 mol) of 6-(3,4-dimethoxyphenyl)-5-hydroxymethyl-2,3,4,5-tetrahydropyridazin-3-one are added with stirring. After a reaction time of 5 hours, the mixture is concentrated at room temperature and the residue is worked up as in Example 5.

Yield: 8.1 g (75% of theory). Melting point: 150°–151° C. Elemental analysis: $C_{21}H_{21}ClN_2O_6$ (432.86); calculated: (%) C 58.3, H 4.9, Cl 8.2, N 6.5, O 22.2; found: (%) C 58.3, H 4.8, Cl 8.3, N 6.3, O 22.1.

EXAMPLE 7

6-(4-Acetylaminophenyl)-5-hydroxymethyl-2-methyl-2,3,4,5-tetrahydropyridazin-3-one 7.4 g (0.03 mol) of 4-(4-acetylaminophenyl)-carbonyl-γ-butyrolactone and 2 ml (0.038 mol) of methylhydrazine in 30 ml of ethanol are heated at room temperature for 1 hour and then under reflux for 3 hours. After the mixture has been cooled, the precipitated product is filtered off with suction and washed.

Yield: 4.6 g (56% of theory). Melting point: 219°–221° C. Elemental analysis: $C_{14}H_{17}N_3O_3$ (275.31); calculated: (%) C 61.1, H 6.2, N 15.3, O 17.4; found: (%) C 61.0, H 5.9, N 15.4, O 17.7.

EXAMPLE 8

6-(6-Acetylaminophenyl)-5-hydroxymethyl-2-phenyl-2,3,4,5-tetra-hydropyridazin-3-one 4.7 g (0.019 mol) of 4-(4-acetylaminophenyl)-carbonyl-butyrolactone and 2 ml (0.02 mol) of phenylhydrazine are stirred in 30 ml of ethanol at room temperature for 1 hour and then under reflux for 16 hours. The precipitated product is filtered off with suction and recrystallised from 90% strength ethanol.

Yield: 1.0 g (16% of theory) Melting point: 221°–222° C. Elemental analysis: $C_{19}H_{19}N_3O_3$ (337.38); calculated: (%) C 67.6, H 5.7, N 12.5, O 14.2; found: (%) C 67.5, H 5.9, N 12.6, O 14.1.

EXAMPLE 9

2,3,4,5-Tetrahydro-6-(2-furyl)-5-hydroxymethyl-pyridazin-3-one 4.7 g (0.026 mol) of 4-(2-furyl)-carbonyl-γ-butyrolactone and 1.5 ml (0.03 mol) of hydrazine hydrate are dissolved in 40 ml of ethanol at room temperature and stirred at 50° C. for 1 hour. After the mixture has been concentrated, the reaction product is subjected to fractionation by chromatography over a silica gel column using methylene chloride/methanol=9:1 as the mobile phase.

Yield: 1.4 g (28% of theory). Melting point: 161°–163° C. Elemental analysis: $C_9H_{10}N_2O_3$ (194.19); calculated: C 55.7, H 5.2, N 14,4, O 24.7; found: C 55.6, H 4.9, N 14.4, O 25.0.

EXAMPLE 10

(a) 4-(2-Pyrrolyl)-carbonyl-γ-butyrolactone hydrazone hydrate 7.2 g (0.04 mol) of 4-(2-pyrrolyl)-carbonyl-γ-butyrolactone and 2.5 ml (0.05 mol) of hydrazine hydrate are stirred in ethanol at room temperature for 4 hours. The product which has crystallised out is filtered off with suction and rinsed with ethanol.

Yield: 7.0 g (83% of theory). Melting point: 140°–142° C. Elemental analysis: $C_9H_{13}N_3O_3$ (211.22); calculated: C 51.2, H 6.2, N 19.9, O 22.7; found: C 51.0, H 6.2, N 20.0, O 23.0.

(b) 2,3,4,5-Tetrahydro-5-hydroxymethyl-6-(2-pyrrolyl)-pyridazin-3-one 5.2 g (0.025 mol) of the compound prepared in section (a) are heated under reflux with 50 ml of ethanol containing 1 drop of ethanolic hydrochloric acid for 90 minutes. After the mixture has been concentrated, the residue is triturated with petroleum ether, whereupon it crystallises. The resulting crude crystals are filtered off with suction and recrystallised from ethanol.

Yield: 2.2 g (46% of theory). Melting point: 202°–203° C. Elemental analysis: $C_9H_{11}N_3O_2$ (193.21); calculated: C 56.0, H 5.7, N 21.7, O 16.6; found: C 56.4, H 5.9, N 21.9, O 16.5.

EXAMPLE 11

2,3,4,5-Tetrahydro-5-hydroxymethyl-6-(3-nitrophenyl)-pyridazin-3-one 3.5 g (0.015 mol) of 4-(3-nitrophenyl)-carbonyl-γ-butyrolactone and 0.8 ml (0.016 mol) of hydrazine hydrate are heated at room temperature for 30 minutes and then under reflux for 60 hours. After the mixture has been concentrated, the residue is subjected to fractional crystallisation from ethyl acetate/petroleum ether.

Yield: 1.1 g (30% of theory). Melting point: 246°–248° C. Elemental analysis: $C_{11}H_{11}N_3O_4$ (249.23); calculated: C 53.0, H 4.4, N 16.9, O 25.7; found: C 53.0, H 4.6, N 16.8, O 26.0.

EXAMPLE 12

2,3,4,5-Tetrahydro-5-hydroxymethyl-6-(3-indolyl)-pyridazin-3-one 3.3 g (0.014 mol) of 4-(3-indolyl)-carbonyl-γ-butyrolactone and 0.85 ml (0.018 mol) of hydrazine hydrate are stirred in 50 ml of ethylene glycol monomethyl ether and 1 ml of acetic acid at 80° C. for 18 hours. After 10 ml of petroleum ether have been added to the reaction mixture, the product crystallises with a good purity.

Yield: 1.2 g (35% of theory). Melting point: 235°–237° C. Elemental analysis: $C_{13}H_{13}N_3O_2$ (243.27) calculated: C 64.2, H 5.4, N 17.3, O 13.2; found: C 63.8, H 5.3, N 17.1, O 13.5.

EXAMPLE 13

2,3,4,5-Tetrahydro-5-hydroxymethyl-6-(4-(2-(1-imidazolyl)-ethoxy)-phenyl)-pyridazin-3-one 5.2 g (0.017 mol) of 4-(4-(2-(1-imidazolyl)-ethoxy)-phenyl)-carbonyl-γ-butyrolactone and 1 ml (0.02 mol) of hydrazine hydrate are stirred in 30 ml of ethanol at room temperature for 1 hour and then at 60° C. for 16 hours. After the mixture has been cooled, 15 ml of ether are added and the precipitated product is filtered off with suction, washed with either and dried.

Yield: 2.7 g (51% of theory). Melting point: 199°–200° C. Elemental analysis: $C_{16}H_{18}N_4O_3$ (314.35); calculated: C 61.1, H 5.8, N 17.8, O 15.3; found: C 61.5, H 5.6, N 18.1, O 15.1.

EXAMPLE 14

6-(4-Methoxyphenyl)-5-(hydroxymethyl-2,3,4,5-tetrahydro-pyridazin-3-one 9.4 g (0.043 mol) of 4-(4-methoxyphenyl-carbonyl)-γ-butyrolactone and 4 g (0.08 mol) of hydrazine hydrate are heated under reflux in 80 ml of ethanol for 6 hours. After the mixture has been concentrated, the residue is recrystallised from water.

Yield: 2.5 g (25% of theory). Melting point: 154°–156° C. Elemental analysis: $C_{12}H_{14}N_2O_3$ (234.26); calculated: C 61.5, H 6.0, N 12.0, O 20.5; found: C 62.0, H 6.1, N 11.6, O 20.5.

EXAMPLE 15

6-(2-Thienyl)-5-hydroxymethyl-2,3,4,5-tetrahydro-pyridazin-3-one 11.8 g (0.06 mol) of 4-(2-thienyl-carbonyl)-γ-butyrolactone and 3.1 g (0.062 mol) of hydrazine hydrate are stirred in 100 ml of ethanol at room temperature for 2 hours. The precipitated hydrazone is filtered off with suction, 60 ml of toluene and 6 ml of acetic acid are added and the mixture is heated under reflux for 2 hours. After the mixture has been cooled, the precipitated product is filtered off with suction, washed and dried.

Yield: 3.6 g (29% of theory). Melting point: 160°–162° C. Elemental analysis: $C_9H_{10}N_2O_2S$ (210.19); calculated: C 51.4, H 4.8, N 13.3, O 15.2, S 15.2; found: C 50.9, H 4.8, N 13.4, O 15.4, S 15.2.

EXAMPLE 16

6-(4-(5-Methyl-1,3,4-oxdiazol-2-yl)-methoxyphenyl)-5-hydroxymethyl-2,3,4,5-tetrahydro-pyridazin-3-one 9.0 g (0.03 mol) of 4-(4-(5-methyl-1,3,4-oxdiazol-2-yl)-methoxy-phenyl-carbonyl)-γ-butyrolactone and 1.6 g (0.032 mol) of hydrazine hydrate are stirred in 50 ml of ethanol at room temperature for 12 hours. After addition of 5 ml of acetic acid, the mixture is heated under reflux for 2 hours and concentrated, the residue is dissolved in ethyl acetate and the solution is extracted with aqueous potassium carbonate solution. The organic phase is concentrated and the residue is crystallised with methylene chloride.

Yield: 6 g (64% of theory). Melting point: 134°–136° C. Elemental analysis: $C_{15}H_{16}N_4O_4$ (316.32); calculated: C 57.0, H 5.1, N 17.7, O 20.2; found: C 56.7, H 5.3, N 17.2, O 21.3.

EXAMPLE 17

6-(4-(1-Pyrrolidin-2-onyl)-phenyl)-5-hydroxymethyl-2,3,4,5-tetrahydro-pyridazin-3-one 8.4 g (0.031 mol) of 4-(4-(1-pyrrolidin-2-onyl)-phenyl-carbonyl)-γ-butyrolactone and 1.7 g (0.034 mol) of hydrazine hydrate are stirred in 50 ml of ethanol at 50° C. for 2 hours, the mixture is cooled and the precipitate is filtered off with suction. The resulting hydrazone is heated under reflux with 70 ml of ethanol and 5 ml of acetic acid for 2 hours, the mixture is cooled and the precipitate is filtered off with suction and dried.

Yield: 4.2 g (48% of theory). Melting point: 219°–220° C. Elemental analysis: $C_{15}H_{17}N_3O_3$ (287.32); calculated: C 62.7, H 6.0, N 14.6, O 16.7; found: C 62.1, H 6.4, N 14.5, O 17.5.

EXAMPLE 18

6-(4-(2-Methoxyethoxy)-phenyl)-5-hydroxymethyl-2,3,4,5-tetrahydro-pyridazin-3-one 13.7 g (0.052 mol) of 4-(4-(2-methoxyethoxy)-phenylcarbonyl)-γ-butyrolactone are reacted with 2.8 g (0.056 mol) of hydrazine hydrate in 80 ml of ethanol as described above.

Yield: 12.5 g (87% of theory). Melting point: 187°–188° C. Elemental analysis: $C_{14}H_{18}N_2O_4$ (278.31); calculated: C 60.4, H 6.5, N 10.1, O 23.0; found: C 60.9, H 7.0, N 10.2, O 21.8.

EXAMPLE 19

6-(4-(3-Pyridyl-methoxyl-phenyl)-5-hydroxymethyl-2,3,4,5-tetrahydro-pyridazin-3-one 7.5 g (0.025 mol) of 4-(4-(3-pyridyl-methoxy)-phenylcarbonyl-γ-butyrolactone are reacted with 1.4 g (0.028 mol) of hydrazine hydrate in 50 ml of ethanol, as described above.

Yield: 6.4 g (82% of theory). Melting point: 222°–223° C. Elemental analysis: $C_{17}H_{17}N_3O_3$ (311.34); calculated: C 65.6, H 5.5, N 13.5, O 15.4; found: C 65.8, H 5.4, N 13.8, O 15.1.

EXAMPLE 20

6-(4-(4-Methyl-2-pyridon-6-yl)-methoxy-phenyl)-5-hydroxymethyl-2,3,4,5-tetrahydro-pyridazin-3-one 6 g (0.018 mol) of 4-((4-methyl-2-pyridon-6-yl)-methoxyphenyl)-carbonyl-γ-butyrolactone and 1 g (0.02 mol) of hydrazine hydrate are reacted in 50 ml of ethanol, as described above.

Yield: 5.4 g (88% of theory). Melting point: 65°–68° C. Elemental analysis: $C_{18}H_{19}N_3O_4$ (341.37); calculated: C 63.3, H 5.6, N 12.3, O 18.7; found: C 62.8, H 5.3, N 12.5, O 19.2.

EXAMPLE 21

6-(4-Methylmercaptophenyl)-5-hydroxymethyl-2,3,4,5-tetrahydro-pyridazin-3-one 10.6 g (0.045 mol) of 4-(4-methylmercaptophenyl)-carbonyl-γ-butyrolactone are stirred in 70 ml of ethanol with 2.5 g (0.05 mol) of hydrazine hydrate at room temperature for 90 minutes. After addition of 8 ml of acetic acid, the mixture is heated under reflux for 1 hour and cooled and the precipitate is filtered off with suction and dried.

Yield: 7.1 g (63% of theory). Melting point: 158°–160° C. Elemental analysis: ($C_{12}H_{14}N_2O_2S$) (250.32); calculated: C 57.6, H 5.6, N 11.2, O 12.8, S 12.8; found: C 57.8, H 5.6, N 11.1, O 12.9, S 12.7.

EXAMPLE 22

6-(4-(2-Methoxyethyl-aminocarbonylmethoxy)-phenyl)-5-hydroxymethyl-2,3,4,5-tetrahydropyridazin-3-one 4.0 g (0.012 mol) of 4-(4-(2-methoxyethylamino-carbonylmethoxy)-phenyl-carbonyl-γ-butyrolactone and 0.7 g (0.014 mol) of hydrazine hydrate are reacted in 20 ml of ethanol, as described above.

Yield: 2.1 g (52% of theory). Melting point: 169°–171° C. Elemental analysis: ($C_{16}H_{21}N_3O_5$) (335.36); calculated: C 57.3, H 6.3, N 12.5, O 23.9; found: C 57.0, H 6.0, N 12.4, O 24.5.

EXAMPLE 23

6-(4-(Aminocarbonylmethoxy)-phenyl)-5-hydroxymethyl-2,3,4,5-tetrahydropyridazin-3-one 11.3 g (0.043 mol) of 4-(4-(aminocarbonylmethoxy)-phenyl)-carbonyl-γ-butyrolactone and 2.4 g (0.048 mol) of hydrazine hydrate are reacted in 70 ml of ethanol, as described above.

Yield: 6.5 g (55% of theory). Melting point: 238°–240° C. Elemental analysis: ($C_{13}H_{15}N_3O_4$) (277.28); calculated: C 56.3, H 5.5, N 15.2, O 23.1; found: C 55.5, H 5.9, N 15.6, O 24.0.

EXAMPLE 24

6-(3,4-Dimethoxyphenyl)-5-hydroxymethyl-2-methyl-2,3,4,5-tetrahydropyridazin-3-one 7.5 g (0.03 mol) of 4-(3,4-dimethoxyphenyl)-carbonyl-γ-butyrolactone and 2 ml (0.03 mol) of methylhydrazine are stirred in 50 ml of ethanol at room temperature for 1 hour and then at 90° C. for 17 hours. After the mixture has been cooled, the precipitated product is filtered off with suction and dried.

Yield: 4.3 g (52% of theory). Melting point: 158°–160° C. Elemental analysis: ($C_{14}H_{18}N_2O_4$) (278.31); calculated: C 60.4, H 6.5, N 10.1, O 23.0; found: C 60.2, H 6.6, N 10.2, O 23.0.

EXAMPLE 25

6-(4-Cyanophenyl)-5-hydroxymethyl-2,3,4,5-tetrahydropyridazin-3-one 3.0 g (0.014 mol) of 4-(4-cyanophenyl)-carbonyl-γ-butyrolactone and 1 ml (0.021 mol) of hydrazine hydrate are stirred in 50 ml of ethanol and 50 ml of dimethylformamide at room temperature for 10 hours. After addition of 1 ml of acetic acid, the mixture is stirred at 80° C. for 18 hours and worked up as above.

The product is crystallised by addition of 2 ml each of diethyl ether, petroleum ether and ethyl acetate.

Yield: 1.2 g (38% of theory). Melting point: 183°–186° C. Elemental analysis: ($C_{12}H_{11}N_3O_2$) (229.24); calculated: C 62.9, H 4.8, N 18.3, O 14.0; found: C 61.9, H 4.9, N 17.7, O 14.12.

EXAMPLE 26

6-((4-Hydroxycarbonylmethoxy)-phenyl)-5-hydroxymethyl-2,3,4,5-tetrahydropyridin-3-one 6.5 g (0.025 mol) of 4-(4-(hydroxycarbonylmethoxy)-phenyl)-carbonyl-γ-butyrolactone and 2.8 g (0.056 mol) of hydrazine hydrate are stirred in 50 ml of ethanol at room temperature for 3 hours. After addition of 8 ml of acetic acid, the mixture is heated under reflux for 1 hour and cooled and the precipitate is filtered off with suction and dried.

Yield: 6.8 g (99% of theory). Melting point: 187° C. Elemental analysis: ($C_{13}H_{14}N_2O_5$) (278.27); calculated: C 56.1, H 5.1, N 10.1, O 28.7; found: C 56.0, H 5.2, N 10.2, O 28.9.

EXAMPLE 27

(a)

4-(3,4,5-Trimethoxyphenyl)-carbonyl-γ-butyrolactone hydrazone hydrate 11.2 g (0.04 mol) of 4-(3,4,5-trimethoxyphenyl)-carbonyl-γ-butyrolactone and 2 ml (0.04 mol) of hydrazine hydrate are stirred in 60 ml of ethanol at room temperature for 1 hour and the precipitate is filtered off with suction.

Yield: 10.5 g (84% of theory). Melting point: 154°–157° C.

(b)

2,3,4,5-Tetrahydro-5-hydroxymethyl-6-(3,4,5-trimethoxy-phenyl)-pyridazin-3-one 7.0 g (0.222 mol) of the compound prepared in section (a) are stirred in 20 ml of dimethylformamide and 1 ml of acetic acid at 80° C. for 5 hours. After the mixture has been concentrated, the residue is taken up in methylene chloride, the methylene chloride mixture is washed with potassium carbonate solution and concentrated and the residue is recrystallised from ethanol.

Yield: 4.0 g (61% of theory). Melting point: 173°–175° C. Elemental analysis: ($C_{14}H_{18}N_2O_5$) (294.31); calculated: C 57.1, H 6.2, N 9.5, O 27.2; found: C 57.0, H 5.8, N 9.7, O 27.9.

EXAMPLE 28

4-(3-Indolyl)-carbonyl-γ-butyrolactone

This compound, used as the starting material for the above Example 12, is prepared as follows:

21.7 g (0.1 mol) of 4-(3-indolyl)-4-oxo-butyric acid, 8 ml of 39% strength formaldehyde solution and 130 ml of 3.5% strength sodium hydroxide solution are stirred in an autoclave at 50° C. for 24 hours. After addition of 10 ml of concentrated hydrochloric acid, stirring is continued at room temperature for 12 hours, the mixture is extracted with methylene chloride, the extract is washed with sodium bicarbonate solution and concentrated and the residue is recrystallised from toluene.

Yield: 10.4 g (45% of theory). Melting point: 188°–191° C. Elemental analysis: $C_{13}H_{11}NO_3$ (229.24); calculated: C 68.1, H 4.8, N 6.1, O 20.9; found: C 67.7, H 4.9, N 6.3, O 20.8.

Further 4-aryl-carbonyl-γ-butyrolactones can be prepared in an analogous manner, for example:
4-(3-nitrophenyl)-carbonyl-γ-butyrolactone,
4-(1-acetyl-2-pyrrolidinyl)-carbonyl-γ-butyrolactone,
4-(1-formyl-2-pyrrolidinyl)-carbonyl-γ-butyrolactone,
4-(2-pyrrolidinyl)-carbonyl-γ-butyrolactone,
4-(2-pyrrolyl)-carbonyl-γ-butyrolactone,
4-(2-furyl)-carbonyl-γ-butyrolactone,
4-(4-cyanophenyl)-carbonyl-γ-butyrolactone,
4-(4-methoxycarbonylphenyl)-carbonyl-γ-butyrolactone,
4-(4-nitrophenyl)-carbonyl-γ-butyrolactone,
4-(4-aminocarbonylaminophenyl)-carbonyl-γ-butyrolactone,
4-(4-(2-(1-imidazolyl)-ethoxy)-phenyl)-carbonyl-γ-butyrolactone,
4-(4-(2-oxo-1,3-oxazolidin-5-yl)-methoxyphenyl)-carbonyl-γ-butyrolactone and
4-(4-(1,4-dioxobutyleneimino)-phenyl)-carbonyl-γ-butyrolactone.

The following examples illustrate the composition of formulations of the tetrahydropyridazinone derivatives according to the invention.

EXAMPLE A

Tablets

|  | per tablet |
|---|---|
| Active compound (finely ground) | 50 mg |
| Lactose (powdered) | 150 mg |
| Maize starch, white | 230 mg |
| Polyvinylpyrrolidone | 15 mg |
| Magnesium stearate | 5 mg |
|  | 450 mg |

EXAMPLE B

Injection solution

| Active compound | 4 mg |
|---|---|
| Sodium chloride | 0.7 mg |
| Water for injection purposes | to 1 ml |

EXAMPLE C

Rectal medicament form

| Active compound | 20 mg |
|---|---|
| Suppository base | to 2 g |

EXAMPLE D

Emulsions

| Active compound | 60 mg |
|---|---|
| Glycerol, pure | 0.2–2.0 g |
| Polyethylene stearate | q.s. |
| Neutral oil | q.s. |
| Flavour correctant | q.s. |
| Demineralised water | to 100 ml |

EXAMPLE E

Active compound solutions

| Active compound | 8 mg |
|---|---|
| Polyethylene glycol | 1.5 mg |
| Glycofurol | to 4 ml |
| Diluent: | 6 ml |
| Water for injection purposes |  |

The tetrahydropyridazinone derivatives of the invention display, even at low dosages, a therapeutically particularly valuable combination of antithrombotic, cardiotonic and antianginal effects with a slight lowering of the blood pressure.

The following tables 1 to 5 show the effective data of compounds of the invention obtained in different in vivo and in vitro tests.

The values of the arterial thrombotic protection given in table 1 were determined in rats according to the method of Meng and Seuter (Naunyn-Schmiedeberg's Arch. Pharmacol. 301, 115 (1977)), those of the venous thrombotic protection were determined in rabbits according to the Harbauer method ("Versuche zur Entwicklung eines standardisierten venösen Thrombosemodells am Kaninchen" ("Tests for developing a standardized venous thrombotic model in rabbits"), 17th Angiologic Symposium, Kitzbühel (1982)).

The values of Table 2 showing the influence on the action of arachidonic acid were determined in guinea pigs under anesthesia using the Lefort and Vargaftig method (Br. J. Pharmac. 63, 35 (1978)).

The values of tables 3 to 5 showing the inhibition of the thrombocytic aggregation were determined in vitro according to the Born method (J. Physiol. 162 67 P (1962)) using arachidonic acid, thrombin or adenosine diphosphate as aggregation agent.

TABLE 1

Influence on the experimental thrombosis in vivo

| R | Dose mg/kg i.p. | Thrombotic Protection % arterial (rat) | venous (rabbit) |
|---|---|---|---|
|  | 10 |  | 57 |
|  | 10 |  | 50 |
|  | 0.3<br>1 | 30<br>80 | 60<br>78 |
|  | 3<br>10 |  | 57<br>86 |
|  | 10. |  | 83 |
|  | 0.5<br>1 | 50 | 50 |
|  | 1 |  | 42 |
|  | 1<br>3 | 33 | 57 |

TABLE 2

Influence on the action of arachidonic acid (arachidonic acid 500 g/kg i.v.) in vivo in guinea pigs under anesthesia

| R | R² | R¹ | Dose mg/kg i.v. | TXA₂ Effect Broncho-spasm | TXA₂ Effect Thrombo-cytopenia | PGI₂ Effect Lowering of blood pressure |
|---|---|---|---|---|---|---|
| phenyl | H | H | 1-10 | (+) | — | (+) |
| 4-CH₃-phenyl | H | H | 1-10 | (+) | (+) | (+) |
| 4-CH₃O-phenyl | H | H | 1-10 | (+) | — | ++ |
| 4-Cl-phenyl | H | H | 1-10 | (+) | (+) | (+) |
| 3-O₂N-phenyl | H | H | 1-10 | ++ | + | (+) |
| CH₃-C(=N-N=)-CH₂-O-phenyl (3-methyl-5-(phenoxymethyl)-triazole) | H | H | 1-10 | ++ | ++ | + |
| 3,4-(CH₃O)₂-phenyl | H | 3-pyridinyl-C(=O)-CH₂- | 1-10 | (+) | (+) | — |
| 4-(CH₃-C(=O)-NH)-phenyl | CH₃ | H | 1-10 | (+) | (+) | (+) |
| 4-(2-oxo-pyrrolidin-1-yl)-phenyl | H | H | 0.3-3 | + | ++ | + |
| 2-pyrrolyl | H | H | 1-10 | ++ | +++ | (+) |

TABLE 2-continued

Influence on the action of arachidonic acid (arachidonic acid 500 g/kg i.v.) in vivo in guinea pigs under anesthesia

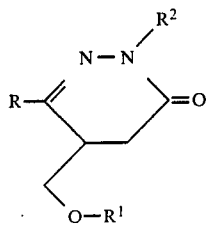

| R | R² | R¹ | Dose mg/kg i.v. | TXA₂ Effect Broncho-spasm | TXA₂ Effect Thrombo-cytopenia | PGI₂ Effect Lowering of blood pressure |
|---|----|----|-----------------|---------------------------|-------------------------------|----------------------------------------|
| 4-methyl-6-(4-methylphenoxymethyl)-2-pyridone-yl | H | H | 1–10 | (+) | (+) | − |
| 4-(acetamido)phenyl | H | H | 0.1–1 | ++ | ++ | ++ |
| 4-[2-(imidazol-1-yl)ethoxy]phenyl | H | H | 1–10 | + | ++ | (+) |
| furan-2-yl | H | H | 1–10 | (+) | (+) | − |
| thiophen-2-yl | H | H | 3–10 | (+) | (+) | (+) |
| 3,4-dimethoxyphenyl | H | H | 0.3–3 | ++ | ++ | +++ |
| indol-3-yl | H | H | 1–10 | + | +++ | (+) |
| 3,4-dimethoxyphenyl | H | 4-chlorophenoxyacetonyl | 1–10 | (+) | − | + |

TABLE 2-continued

Influence on the action of arachidonic acid (arachidonic acid 500 g/kg i.v.) in vivo in guinea pigs under anesthesia

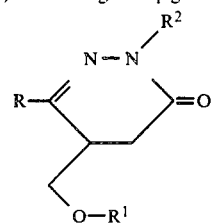

| R | R² | R¹ | Dose mg/kg i.v. | TXA₂ Effect Broncho-spasm | TXA₂ Effect Thrombo-cytopenia | PGI₂ Effect Lowering of blood pressure |
|---|---|---|---|---|---|---|
| 3-pyridylmethyl-O-phenyl- | H | H | 1–10 | + | + | − |

− = no action
(+) = weak
+ = medium
++ = strong
+++ = very strong

TABLE 3

Inhibition of thrombocyte aggregation in vitro (according to BORN) induced by 0.36 mM of arachidonic acid

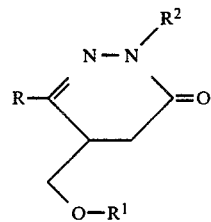

| R | R² | R¹ | IC₅₀ (μM) |
|---|---|---|---|
| phenyl | H | H | 5 |
| 4-CH₃-phenyl | H | H | 4 |
| 4-CH₃O-phenyl | H | H | 1.5 |
| 3-O₂N-phenyl | H | H | 1.5 |
| CH₃-C(=N-N=C(O-CH₂-)-)-O-phenyl | H | H | 1 |

TABLE 3-continued
Inhibition of thrombocyte aggregation in vitro (according to BORN) induced by 0.36 mM of arachidonic acid
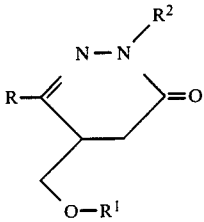
| R | R² | R¹ | IC$_{50}$ (μM) |
|---|---|---|---|
| 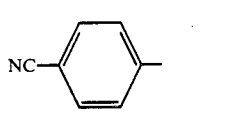 | H | H | 2 |
| 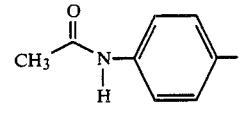 | H | H | 0.3 |
| 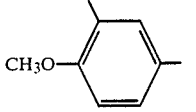 | CH$_3$ | H | >100 |
| 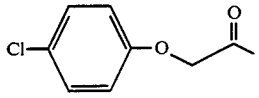 | H | 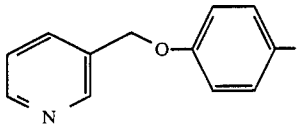 | 4 |
| 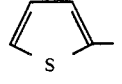 | H | H | 0.45 |
| 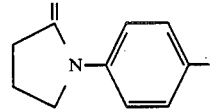 | H | H | 50 |
| 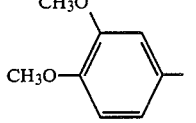 | H | H | 0.4 |
| 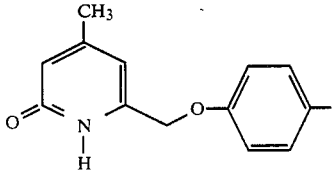 | H | H | 0.6 |
|  | CH$_3$ | H | 15 |

TABLE 3-continued

Inhibition of thrombocyte aggregation in vitro (according to BORN) induced by 0.36 mM of arachidonic acid

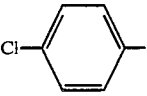

| R | R² | R¹ | IC₅₀ (μM) |
|---|---|---|---|
| 4-Cl-C₆H₄- | H | H | 0.9 |
| 4-(CH₃CONH)-C₆H₄- | H | H | 0.2 |
| 2,3-(CH₃O)₂-C₆H₃- | CH₃ | H | 40 |
| indol-3-yl | H | H | 0.55 |
| 2,3-(CH₃O)₂-C₆H₃- | H | pyridin-3-yl-C(O)- | 30 |
| 2,3,4-(CH₃O)₃-C₆H₂- | H | H | 6 |

TABLE 4

Inhibition of thrombocyte aggregation in vitro (according to BORN) induced by 0.2–0.4 N.I.H. units/ml

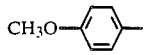

| R | R¹ | IC₅₀ (μM) |
|---|---|---|
| 4-CH₃O-C₆H₄- | H | 2.5 |

TABLE 4-continued

Inhibition of thrombocyte aggregation in vitro (according to BORN) induced by 0.2–0.4 N.I.H. units/ml

| R | R¹ | IC₅₀ (μM) |
|---|---|---|

TABLE 4-continued

Inhibition of thrombocyte aggregation in vitro (according to BORN) induced by 0.2–0.4 N.I.H. units/ml

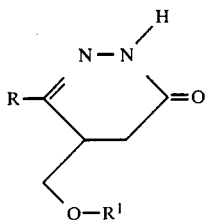

| R | R¹ | IC$_{50}$ (µM) |
|---|---|---|
| 4-Cl-C$_6$H$_4$- | H | 6 |
| 4-(CH$_3$CONH)-C$_6$H$_4$- | H | 0.7 |
| 3,4-(CH$_3$O)$_2$-C$_6$H$_3$- | H | 2 |
| 3,4-(CH$_3$O)$_2$-C$_6$H$_3$- | 4-Cl-C$_6$H$_4$-O-CH$_2$-CO-CH$_3$ (acetonyl) | >100 |

TABLE 5

Inhibition of thrombocyte aggregation in vitro (according to BORN) induced by 10 µM ADP

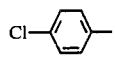

| R | IC$_{50}$ (µM) |
|---|---|
| C$_6$H$_5$- | >100 |
| 4-CH$_3$-C$_6$H$_4$- | 150 |
| 4-CH$_3$O-C$_6$H$_4$- | 50 |
| 4-Cl-C$_6$H$_4$- | 70 |

TABLE 5-continued

Inhibition of thrombocyte aggregation in vitro (according to BORN) induced by 10 µM ADP

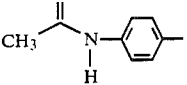

| R | IC$_{50}$ (µM) |
|---|---|
| 4-(CH$_3$CONH)-C$_6$H$_4$- | 10 |
| 3,4-(CH$_3$O)$_2$-C$_6$H$_3$- | 9 |
| CH$_3$-C(=N-N)-O-CH$_2$-...-C$_6$H$_4$- | 20 |
| imidazolyl-CH$_2$CH$_2$-O-C$_6$H$_4$- | 150 |
| 2-oxo-pyrrolidinyl-C$_6$H$_4$- | 20 |
| pyridin-3-yl-CH$_2$-O-C$_6$H$_4$- | 36 |
| N≡C-C$_6$H$_4$- | 20 |

What is claimed is:

1. Tetrahydropyridazinones of the formula I

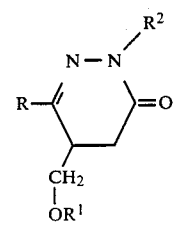

wherein R denotes one of the radicals of the formulae

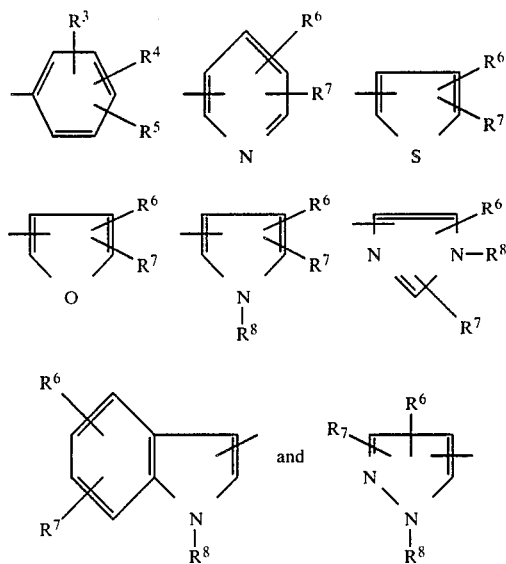

$R^1$ denotes hydrogen; alkyl; aralkyl or acyl of the formula —CO—$R^9$;

$R^2$ denotes hydrogen; alkyl; alkyl mono substituted with a group of the formula —N($R^{17}$)$R^{18}$; phenyl; phenyl substituted with one, two or three substituents selected from the group halogen, alkyl with 1 to 5 C atoms, hydroxy, benzoyloxy, alkylmercapto with 1 to 5 C atoms, amino, monoalkylamino with 1 to 5 C atoms, dialkylamino with a total of 2 to 5 C atoms, alkanoylamino with 1 to 4 C atoms;

$R^3$, $R^4$ and $R^5$ independently of one another denote halogen; alkyl with 1 to 5 C atoms; —OH; alkoxy with 1 to 5 C atoms; alkanoyloxy with 1 to 5 C atoms; benzoyloxy; alkylmercapto with 1 to 5 C atoms; —NH$_2$; monoalkylamino with 1 to 5 C atoms; dialkylamino with a total of 2 to 5 C atoms; or alkanoylamino; $R^3$ and $R^4$ also denote nitro; cyano; alkylsulphoxy or alkylsulphonyl with in each case 1 to 5 C atoms; alkyl($C_1$-$C_5$)-oxycarbonyl or a group of the formula —NR$^{10}$R$^{11}$; the alkyl, alkoxy, monoalkylamino, dialkylamino, alkylmercapto, alkylsulphoxy and alkylsulphonyl radicals $R^3$ and $R^4$ optionally being monosubstituted in the alkyl or alkoxy part by hydroxyl, alkoxy with 1 to 5 C atoms, carboxyl, alkoxycarbonyl with a total of 2 to 7 C atoms, aminocarbonyl of the formula $R^{16}$($R^{15}$)N—CO—, amino, monoalkylamino with 1 to 5 C atoms, dialkylamino with a total of 2 to 6 C atoms, or by a 5-membered or 6-membered heterocyclic radical with 1 to 3 heteroatoms; the 5-membered or 6-membered heterocyclic radical containing one, two or three N atoms, one or two oxygen or sulfur atoms, one nitrogen atom and one oxygen or sulfur atom or containing one oxygen and two nitrogen atoms, the heterocyclic radical optionally containing one N-oxid or S-oxid group and/or containing double bonded oxygen and/or being substituted with one or two alkyl radicals with 1 to 5 C atoms; and $R^4$ and $R^5$ additionally also denote hydrogen;

$R^6$ and $R^7$ independently of one another denote hydrogen; halogen; amino; monoalkylamino with 1 to 5 C atoms; dialkylamino with a total of 2 to 6 C atoms; hydroxyl; alkoxy with 1 to 5 C atoms; alkyl with 1 to 5 C atoms; $R^8$ denotes hydrogen; alkyl with 1 to 5 C atoms; alkanoyl with 1 to 5 C atoms; or benzoyl of the formula

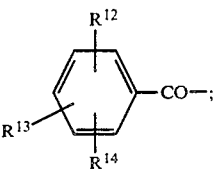

$R^9$ denotes alkyl with 1 to 5 C atoms; pyridyl, alkyl with 1 to 5 C atoms monosubstituted by a phenoxy radical of the formula

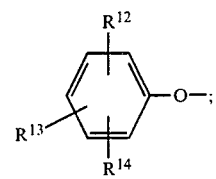

or by a group of the formula

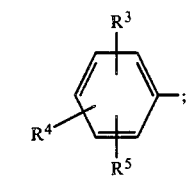

$R^{10}$ denotes alkanoyl with 1 to 5 C atoms; or

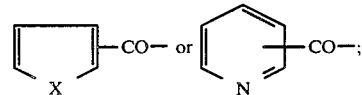

alkanoyl with 1 to 5 C atoms monosubstituted by hydroxy, amino, halogen, alkoxy with 1 to 5 C atoms, or by phenoxy of the formula

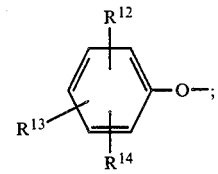

or by benzoyl of the formula

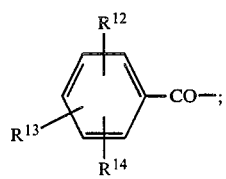

or by a heterocycloalkylcarbonyl of the formula

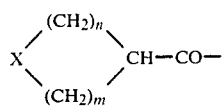

it being possible for the nucleus of the heterocycloalkylcarbonyl to be monosubstituted by alkyl with 1 to 5 C atoms, bromine, or double-bonded oxygen (=O)

$R^{11}$ denotes hydrogen; alkyl with 1 to 5 C atoms; alkanoyl with 1 to 5 C atoms or $R^{10}$ and $R^{11}$ together with the nitrogen to which they are bonded form the radical of a pyrrolidine, piperidine, piperazine, morpholine or thiomorpholine ring or a ring of the formula

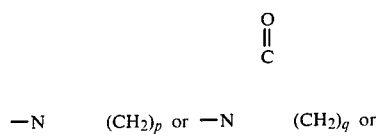

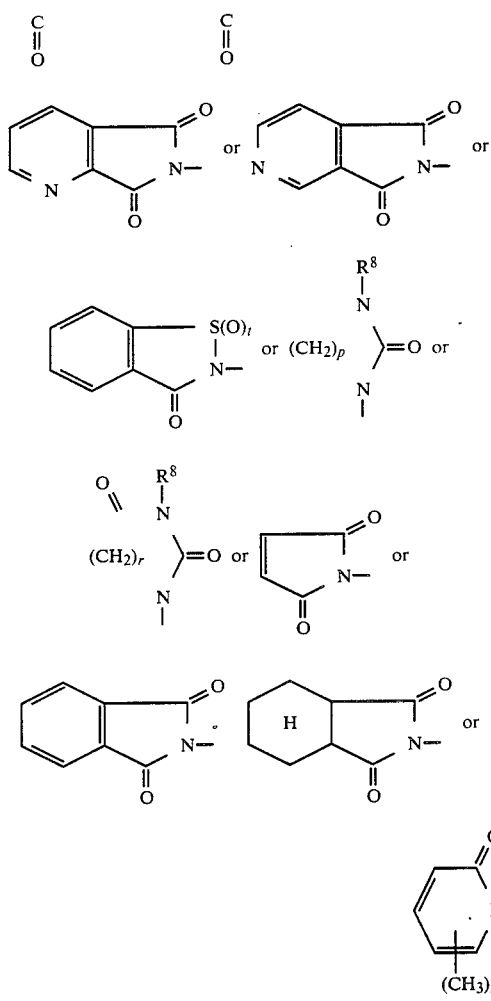

$R^{12}$, $R^{13}$, $R^{14}$ denote hydrogen, alkyl with 1 to 5 C atoms; alkoxy with 1 to 4 C atoms; nitro, cyano; halogen; amino; monoalkylamino with 1 to 5 C atoms; dialkylamino with a total of 2 to 6 C atoms; alkanoylamino with 1 to 5 C atoms or benzoylamino;

$R^{15}$, $R^{16}$ denote hydrogen; alkyl with 1 to 5 C atoms; alkyl with 1 to 5 C atoms monosubstituted with alkoxy with 1 to 4 C atoms, halogen, amino, mono- or dialkylamino with 1 to 4 C atoms in the alkyl groups, or $R^{15}$ and $R^{16}$ together with the N atom to which they are bonded form the radical of a 5-membered or 6-membered heterocyclic ring which optionally contains a further hetero atom from the group consisting of N, O and S;

$R^{17}$, $R^{18}$ denote hydrogen; alkyl with 1 to 6 C atoms, cycloalkyl with 3 to 6 C atoms;

$R^{17}$ and $R^{18}$ together denote a polymethylene chain with 2 to 5 C atoms; a polymethylene chain with 2 to 5 C atoms interrupted by an oxygen or sulphur atom or by a group $=NR^{19}$;

$R^{19}$ denotes hydrogen; alkyl with 1 to 4 C atoms; phenylalkyl with 1 to 3 C atoms in the alkyl group;

X denotes oxygen; sulphur or the group $=N-R^8$;

n denotes 2, 3 or 4;

m, u, t denote 0, 1 or 2;

p denotes 3, 4 or 5;

q denotes 2 or 3;

r denotes 1 or 2, and their acid addition salts,

2. Tetrahydropyridazinones of the formula I

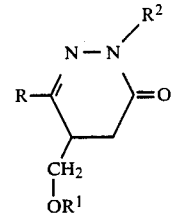

wherein R denotes one of the radicals of the formulae

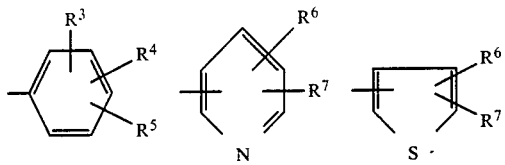

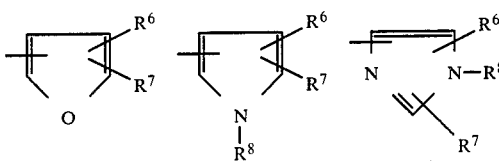

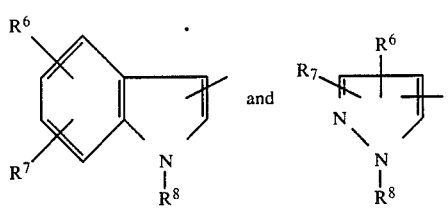

$R^1$ denotes hydrogen; alkyl; aralkyl or acyl of the formula $-CO-R^9$;

$R^2$ denotes hydrogen; alkyl; alkyl mono substituted with a group of the formula $-N(R^{17})R^{18}$; phenyl; phenyl substituted with one, two or three alkyl groups, each having 1 to 5 C atoms;

$R^3$, $R^4$ and $R^5$ independently of one another denote halogen; alkyl with 1 to 5 C atoms; —OH; alkoxy with 1 to 5 C atoms; alkanoyloxy with 1 to 5 C atoms; benzoyloxy; alkylmercapto with 1 to 5 C atoms;

—NH₂; monoalkylamino with 1 to 5 C atoms; dialkylamino with a total of 2 to 5 C atoms; or alkanoylamino with 1 to 4 C atoms; R³ and R⁴ also denote nitro; cyano; alkylsulphoxy or alkylsulphonyl with in each case 1 to 5 C atoms; alkyl(C₁-C₅)-oxycarbonyl or a group of the formula —NR¹⁰R¹¹; the alkyl, alkoxy, monoalkylamino, dialkylamino, alkylmercapto, alkylsulphoxy and alkylsulphonyl radicals R³ and R⁴ optionally being monosubstituted in the alkyl or alkoxy part by hydroxyl, alkoxy with 1 to 5 C atoms, carboxyl, alkoxycarbonyl with a total of 2 to 7 C atoms, aminocarbonyl of the formula R¹⁶(R¹⁵)N—CO—, amino, monoalkylamino with 1 to 5 C atoms, dialkylamino with a total of 2 to 6 C atoms, or by a pyrrol, pyrroline, pyrrolidine, pyrrolidinone, oxazole, oxazoline or oxazolidine radical, or by imidazol-1-yl, imidazol-4-yl, 2-methylimidazol-4-yl, oxadiazol-2-yl, 5-methyl-oxadiazol-2-yl, pyrid-2-, -3- or -4-yl, 2-hydroxy-4-methyl-pyrid-6-yl, 2-pyridone-4-methyl-6-yl, 2-pyrone-4-, -5- or -6-yl or 2-pyrone-4-methyl-6-yl; and R⁴ and R⁵ additionally also denote hydrogen;

R⁶, R⁷, R⁸ denote hydrogen;

R⁹ denotes alkyl with 1 to 5 C atoms; pyridyl; alkyl with 1 to 5 C atoms monosubstituted by a phenoxy radical of the formula

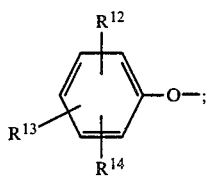

R¹⁰ denotes alkanoyl with 1 to 5 C atoms; alkanoyl with 1 to 5 C atoms monosubstituted by hydroxy, amino, halogen, alkoxy with 1 to 5 C atoms, or by benzoyl;

R¹¹ denotes hydrogen; or

R¹⁰ and R¹¹ together with the nitrogen to which they are bonded form a pyrrolidine, piperidine, piperazine, morpholine or thiomorpholine ring or a ring of the formula

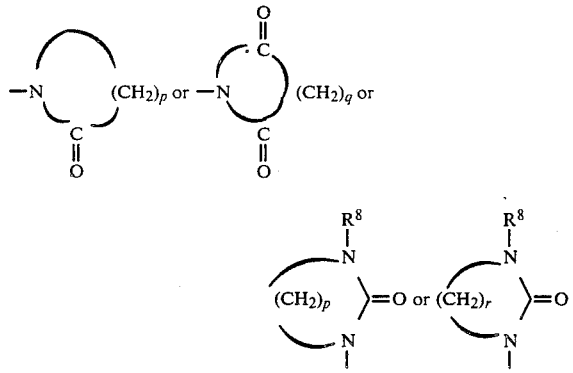

R¹², R¹³, R¹⁴ denote hydrogen; alkyl with 1 to 4 C atoms; alkoxy with 1 to 4 C atoms; halogen;

R¹⁵, R¹⁶ denote hydrogen; alkyl with 1 to 5 C atoms; alkyl with 1 to 5 C atoms monosubstituted with alkoxy with 1 to 4 C atoms, halogen, amino, mono- or dialkylamino with 1 to 4 C atoms in the alkyl groups, or R¹⁵ and R¹⁶ together with the N atom to which they are bonded form the radical of a 5-membered or 6-membered heterocyclic ring which optionally contains a further hetero atom from the group consisting of N, O and S;

R¹⁷, R¹⁸ denote hydrogen; alkyl with 1 to 6 C atoms; R¹⁷ and R¹⁸ together denote a polymethylene chain with 2 to 5 C atoms; a polymethylene chain with 2 to 5 C atoms interrupted by an oxygen or sulphur atom or by a group =NR¹⁹;

R¹⁹ denotes hydrogen; alkyl with 1 to 4 C atoms;

p denotes 3, 4 or 5;

q denotes 2 or 3;

r denotes 1 or 2, and their acid addition salts.

3. Tetrahydropyridazinones of the formula I

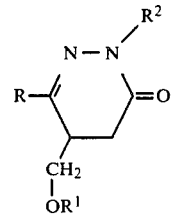

wherein R denotes one of the radicals of the formulae

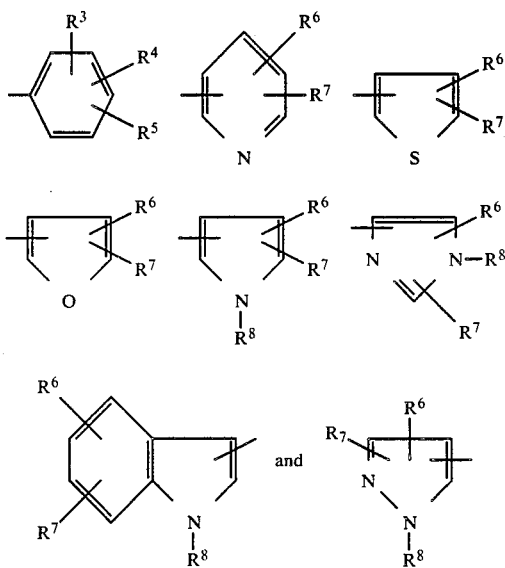

R¹ denotes hydrogen; or acyl of the formula —CO—R⁹;

R² denotes hydrogen; alkyl; phenyl; phenyl substituted with one, two or three alkyl groups each having 1 to 5 C atoms;

R³, R⁴ and R⁵ independently of one another denote halogen; alkyl with 1 to 5 C atoms; —OH; alkoxy with 1 to 5 C atoms; alkanoyloxy with 1 to 5 C atoms; alkylmercapto with 1 to 5 C atoms; —NH₂; dialkylamino with a total of 2 to 5 C atoms; or alkanoylamino with 1 to 4 C atoms; R³ and R⁴ also denote nitro; cyano; or a group of the formula —NR¹⁰R¹¹; the alkyl, alkoxy, dialkylamino, alkylmercapto radicals R³ and R⁴ optionally being monosubstituted in the alkyl or alkoxy part by hydroxyl, alkoxy with 1 to 5 C atoms, aminocarbonyl of the formula R¹⁶(R¹⁵)N—CO—, or by a pyrrol, pyrroline, pyrrolidine, pyrrolidinone, oxazole, oxazoline or oxazolidine radical, or by imidazol-1-yl, imidazol-4-yl, 2-methylimidazol-4-yl, oxadiazol-2-yl, 5-methyloxadiazol-2-yl, pyrid-2-, -3- or -4-yl, 2-hydroxy-4-methyl-pyrid-6-yl, 2-pyridone-4-methyl-6-yl, 2-pyrone-4-, -5- or -6-yl or 2-pyrone-4-methyl-6-yl; and $R^4$ and $R^5$ additionally also denote hydrogen;

$R^6$, $R^7$ and $R^8$ denote hydrogen;

$R^9$ denotes alkyl with 1 to 5 C atoms; pyridyl; alkyl with 1 to 5 C atoms monosubstituted by a phenoxy radical of the formula

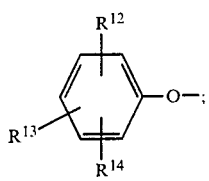

$R^{10}$ denotes alkanoyl with 1 to 5 C atoms; or benzoyl;
$R^{11}$ denotes hydrogen;
$R^{10}$ and $R^{11}$ together with the nitrogen to which they are bonded form the radical of a pyrrolidine, piperidine, piperazine, morpholine or thiomorpholine ring or a ring of the formula

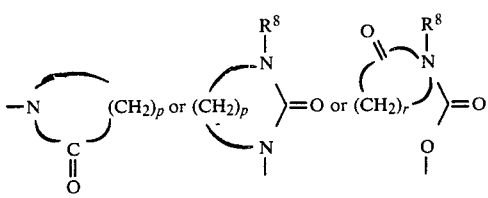

$R^{12}$, $R^{13}$ and $R^{14}$ denote hydrogen; alkyl with 1 to 5 C atoms; alkoxy with 1 to 4 C atoms; halogen;

$R^{15}$, $R^{16}$ denote hydrogen; alkyl with 1 to 5 C atoms; alkyl with 1 to 5 C atoms monosubstituted with alkoxy with 1 to 4 C atoms, or $R^{15}$ and $R^{16}$ together with the N atom to which they are bonded form the radical of a 5-membered or 6-membered heterocyclic ring which optionally contains a further hetero atom from the group consisting of N, O and S;

p denotes 3, 4 or 5;

r denotes 1 or 2, and their acid addition salts.

4. Tetrahydropyridazinones according to claim 1, 2 or 3, characterised in that $R^1$ represents hydrogen; alkyl with 1 or 2 C atoms; alkanoyl with 1 to 3 C atoms; benzoyl or nicotinoyl.

5. Tetrahydropyridazinones according to claim 1, 2 or 3, characterised in that $R^1$ and $R^2$ denote hydrogen.

6. 6-(3,4-Dimethoxyphenyl)-5-hydroxymethyl-2,3,4,5-tetrahydro-pyridazin-3-one.

7. 6-(4-Acetylaminophenyl)-5-hydroxymethyl-2,3,4,5-tetrahydro-pyridazin-3-one.

8. 2,3,4,5-Tetrahydro-5-hydroxymethyl-6-(3-indolyl)-pyridazin-3-one.

9. 2,3,4,5-Tetrahydro-5-hydroxymethyl-6-(4-(2-(1-imidazolyl)-ethoxy)-phenyl)-pyridazin-3-one and its acid addition salts.

10. 6-(4-(5-Methyl-1,3,4-oxdiazol-2-yl)-methoxyphenyl)-5-hydroxymethyl-2,3,4,5-tetrahydro-pyridazin-3-one.

11. 6-(4-Cyanophenyl)-5-hydroxymethyl-2,3,4,5-tetrahydropyridazin-3-one.

12. 6-(4-(1-Pyrrolidin-2-onyl)-phenyl)-5-hydroxymethyl-2,3,4,5-tetrahydro-pyridazin-3-one.

13. Process for the treatment of thromboembolic diseases of the heart and circulatory system comprising administering to the patient a pharmacologically effective dose of a compound of the formula I

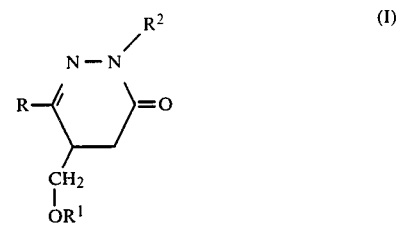

wherein R, $R^1$ and $R^2$ have the meanings given in claim 1.

14. Medicament formulation for the treatment of thromboembolic diseases of the heart and circulatory system containing, besides the customary auxiliaries and excipients used in galenics, an effective dose of a tetrahydropyridazinone of the formula I

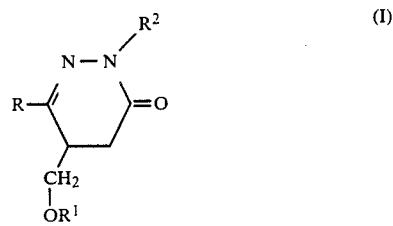

wherein R, $R^1$ and $R^2$ have the meanings given in claim 1.

* * * * *